(12) United States Patent
Lillydahl et al.

(10) Patent No.: US 8,690,800 B2
(45) Date of Patent: Apr. 8, 2014

(54) SYSTEMS AND METHODS FOR REDUCING SUBCONSCIOUS NEUROMUSCULAR TENSION INCLUDING BRUXISM

(76) Inventors: Erik Lillydahl, Boulder, CO (US); Adam Kirell, West Hempstead, NY (US)

( * ) Notice: Subject to any disclaimer, the term of this patent is extended or adjusted under 35 U.S.C. 154(b) by 241 days.

(21) Appl. No.: 13/110,757

(22) Filed: May 18, 2011

(65) Prior Publication Data

US 2011/0288445 A1  Nov. 24, 2011

Related U.S. Application Data

(60) Provisional application No. 61/345,973, filed on May 18, 2010.

(51) Int. Cl.
*A61B 5/117* (2006.01)
*A61B 5/103* (2006.01)
*A61B 5/04* (2006.01)

(52) U.S. Cl.
USPC .......................................... 600/590; 600/546

(58) Field of Classification Search
USPC .................. 600/546, 587, 590, 595
See application file for complete search history.

(56) References Cited

U.S. PATENT DOCUMENTS

| | | | | |
|---|---|---|---|---|
| 6,076,011 A | * | 6/2000 | Hoover | 600/546 |
| 6,270,466 B1 | | 8/2001 | Weinstein et al. | |
| 6,597,944 B1 | * | 7/2003 | Hadas | 600/546 |
| 2009/0131759 A1 | * | 5/2009 | Sims et al. | 600/301 |

OTHER PUBLICATIONS

Beck, Melinda; "Stress So Bad It Hurts—Really," Wall Street Journal—Health Journal, Mar. 17, 2009; D1.
Principato et al.; "Biofeedback Training and Relaxation Exercises for Treatment of Temporomandibular Joint Dysfunction," *Otolaryngology*, Sep.-Oct. 1978; 86(5):766-768.

\* cited by examiner

*Primary Examiner* — Brian Szmal
(74) *Attorney, Agent, or Firm* — Patton Boggs LLP

(57) ABSTRACT

A system for the detection of bruxism includes an electronics housing configured to be worn on the face of a user. The system further includes a first and second sensor, located on a side of the electronics housing. The first and second sensors are secured firmly to the face of the user, positioned a distance apart from each other, and positioned to rest over a muscle of the face; the distance apart being such that the first and second sensors both rest on the muscle of the face. The system also includes a feedback generator, configured to provide feedback to the user when a clenching event occurs. The system also includes a microprocessor, configured to receive a plurality of inputs from the first and second sensors, determine when the clenching event occurs, and activate the feedback generator to provide feedback to the user upon an occurrence of the clenching event.

17 Claims, 27 Drawing Sheets

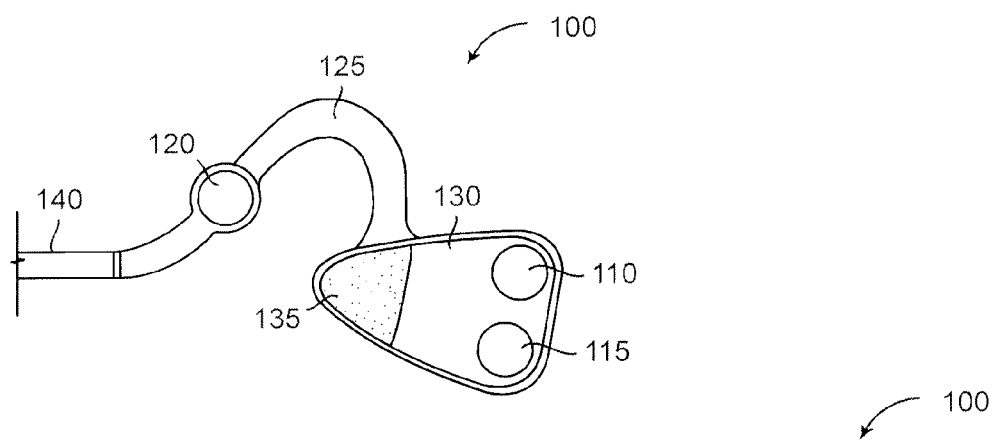
FIG. 1a
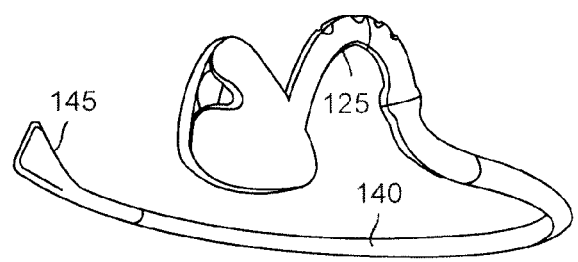
FIG. 1b
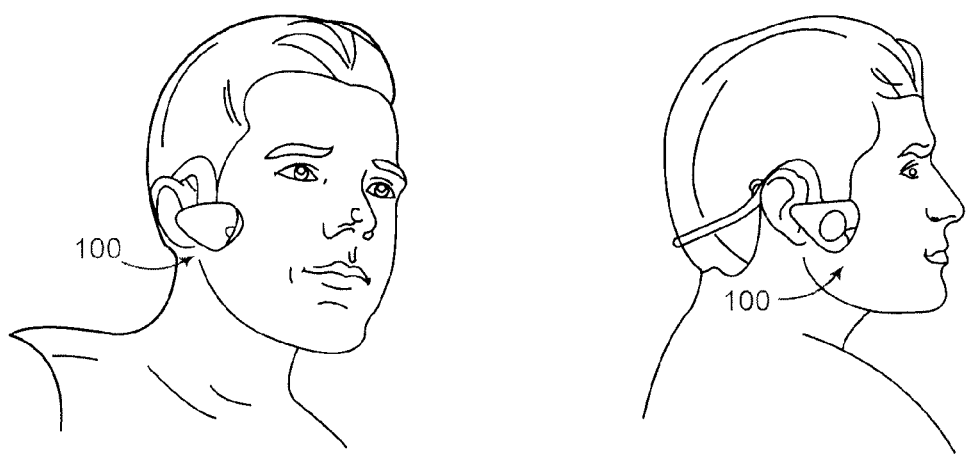
FIG. 1c
FIG. 1d

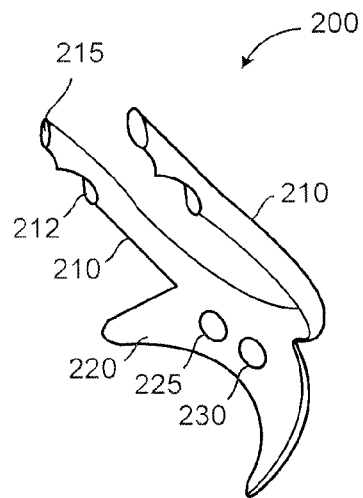
FIG. 2a
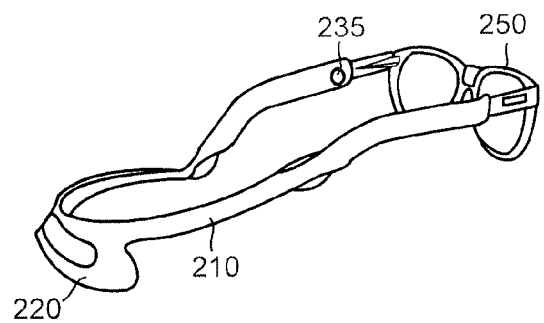
FIG. 2b
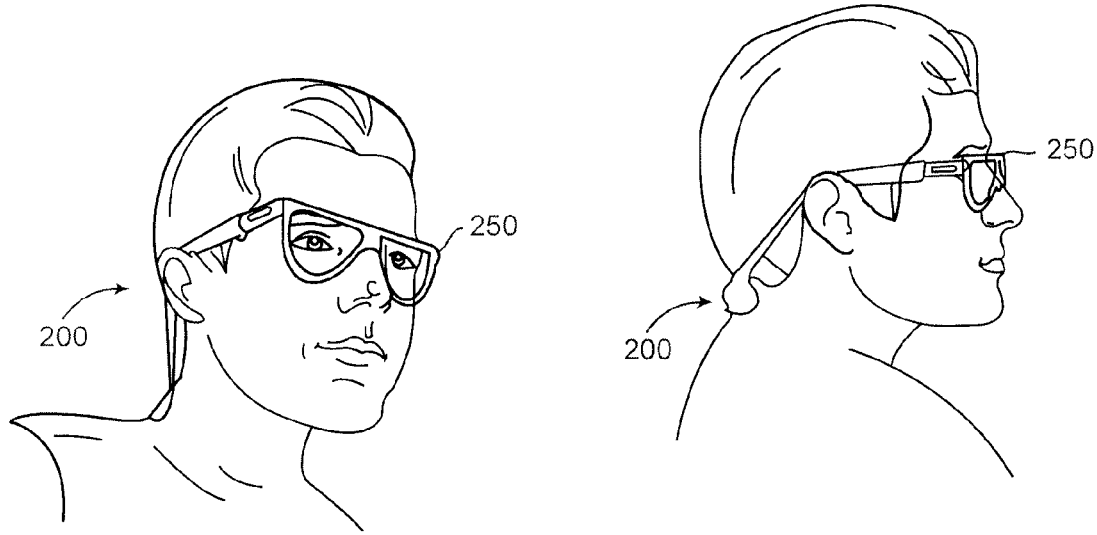
FIG. 2c
FIG. 2d

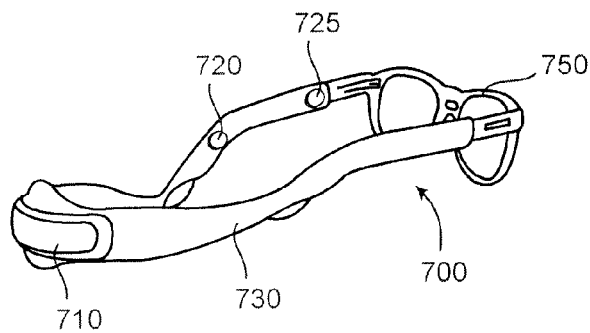
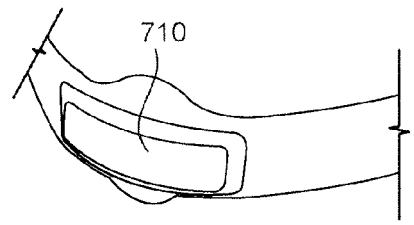
FIG. 7a    FIG. 7b
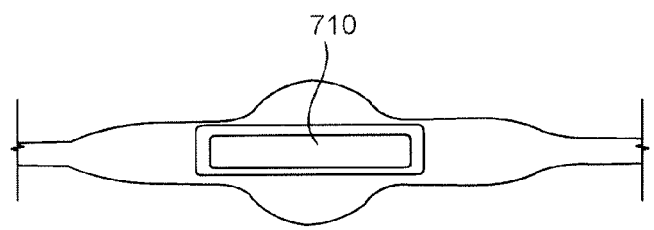
FIG. 7c
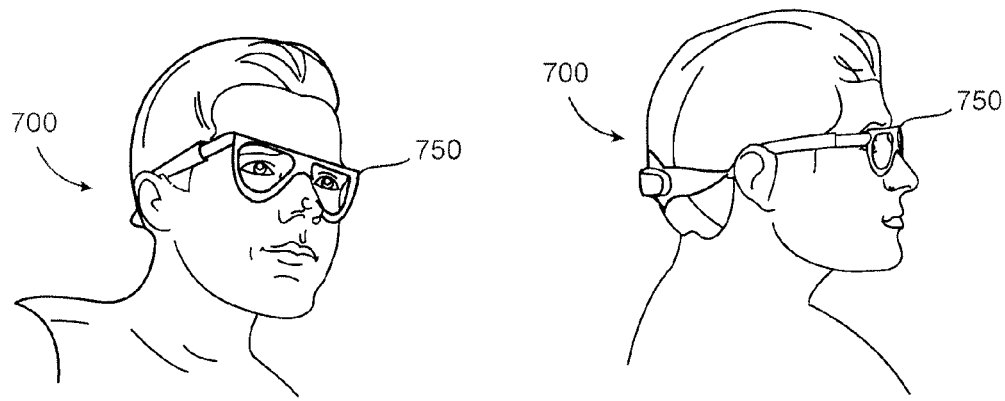
FIG. 7d    FIG. 7e

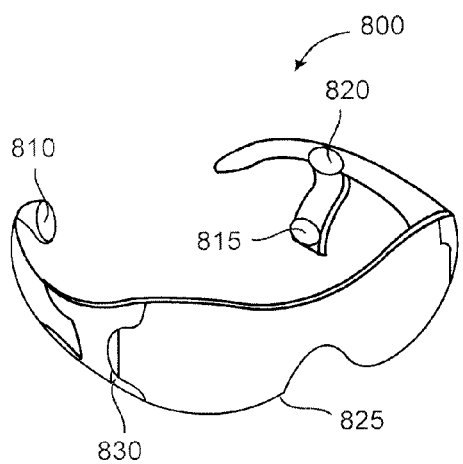
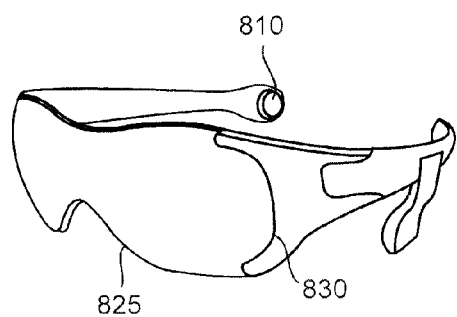
FIG. 8a    FIG. 8b
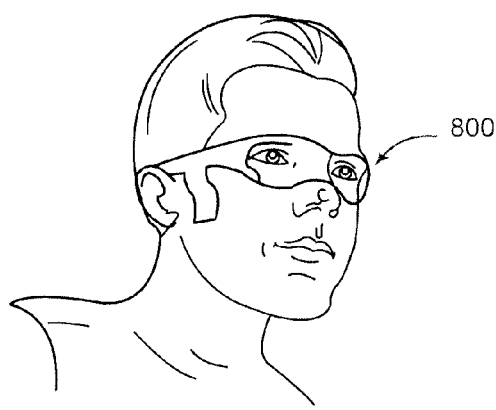
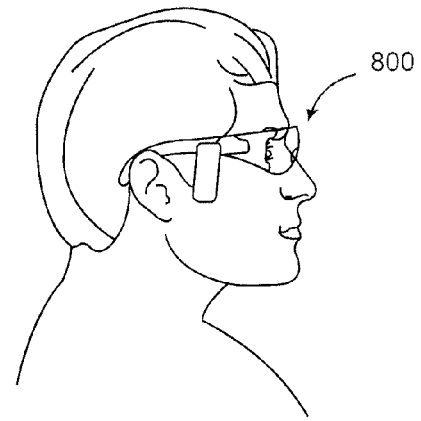
FIG. 8c    FIG. 8d

SYSTEMS AND METHODS FOR REDUCING SUBCONSCIOUS NEUROMUSCULAR TENSION INCLUDING BRUXISM

CROSS REFERENCE TO RELATED APPLICATIONS

This application claims the benefit of U.S. Provisional Application No. 61/345,973, filed May 18, 2010, the entire disclosure of which is incorporated by reference herein.

BACKGROUND

According to the TMJ Association, over 35 million Americans suffer from TMJ (temporomandibular joint) problems. This is a problem involving the jaw joint where the mandible meets the skull, just in front of the ear. It is caused by teeth clenching or grinding (bruxism). In a broader sense, it is a problem with muscle tension of which clenching is one manifestation. Typically the user is unaware that they are tensing their muscles. According to the TMJ Association, "there currently is no treatment that has been proven to work as a preventive measure for TMJ disorders." The demand for such a product is there and growing.

SUMMARY

In one embodiment, a Bruxism Biofeedback device senses the masseter muscle directly, by providing a sensor oriented to fit directly over the masseter muscle of a user.

In one embodiment, a system for the detection of bruxism includes an electronics housing configured to be worn on a face of a user. The system further includes a first and second sensor, located on a side of the electronics housing, such that the first and second sensors are secured firmly to the face of the user, the first and second sensors positioned a distance apart from each other and positioned to rest over a muscle of the face, the distance apart being such that the first and second sensors both rest on the muscle of the face. The system also includes a feedback generator, configured to provide feedback to the user when a clenching event occurs. The system also includes a microprocessor, configured to receive a plurality of inputs from the first and second sensors, determine when the clenching event occurs, and activate the feedback generator to provide the feedback to the user upon an occurrence of the clenching event. Optionally, the system also includes a ground sensor that provides a second plurality of inputs to the microprocessor. In one alternative, the ground sensor is placed a second distance from the first and second sensors, the second distance being greater than the distance between the first and second sensors. Alternatively, the microprocessor includes logic for providing an envelope follower with a high time constant, wherein the logic provides for the determining of the microprocessor. Optionally, the feedback generator is a small unbalanced motor. Optionally, the ground is configured to be located in a location on the face of the user where there are few muscle fibers. Alternatively, the microprocessor includes logic for providing a ring buffer, wherein the ring buffer is used to determine an average for the plurality of inputs, and the average of the plurality of inputs is compared to a threshold to determine the clenching event. In one configuration, the muscle sensed is the masseter muscle. In another configuration, the muscle sensed is the temporalis muscle. In another configuration, the muscle sensed is the Frontalis muscle and/or the procerus muscle. Optionally, the electronics housing includes a wireless network communication system. In one alternative, the wireless network communication system is a Bluetooth communication system. Optionally, the Bluetooth communication system communicates with a device capable of receiving a Bluetooth signal, and the device receiving the Bluetooth signal includes the feedback generator. In one alternative, the device receiving the Bluetooth signal includes the microprocessor. Optionally, the electronics housing includes the first and second sensors but not the microprocessor and feedback generator. In another alternative, the electronics housing includes an adhesive portion for securing the first and second sensors. Optionally, the electronics housing is included as part of a pair of glasses. Optionally, the electronics housing is included as part of a Bluetooth headset.

In one embodiment, a method for the prediction of bruxism includes providing a Bruxism Detection System to a user. The method further includes calibrating the Bruxism Detection System, including having the user clench their teeth while the Bruxism Detection System is worn and in calibration mode. In some alternatives, the user is provided with a manual adjustment mechanism for calibration. The method also includes monitoring the user with the Bruxism Detection System, wherein the monitoring includes smoothing the signal from a plurality of sensors. The method further includes detecting a clenching event and providing feedback to the user based on the detecting. Optionally, the method includes detecting an intensity of an electromyography signal; storing the intensity of the electromyography signal; and setting a clenching event indicator based on the intensity and a time. Optionally, the detecting includes comparing a second electromyography signal to the clenching event indicator.

BRIEF DESCRIPTION OF THE DRAWINGS

FIGS. 1a-1d show one embodiment of a System For Reducing Subconscious Neuromuscular Tension in the form of a headset;

FIGS. 2a-2d show another embodiment of a System For Reducing Subconscious Neuromuscular Tension in the form of a croakie;

FIGS. 7a-7e show another embodiment of a System For Reducing Subconscious Neuromuscular Tension in the form of a croakie;

FIGS. 8a-8d show another embodiment of a System For Reducing Subconscious Neuromuscular Tension in the form of glasses;

FIG. 21b shows a graph of input voltage and output voltage for the envelope follower/detector of FIG. 21a;

DETAILED DESCRIPTION

Figure 3A:
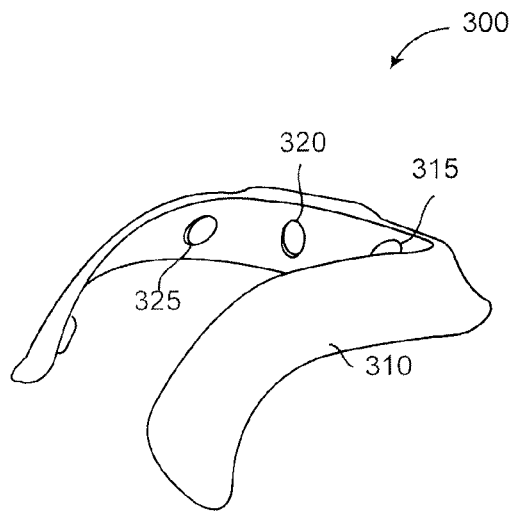
FIGS. 3a-3d show another embodiment of a System For Reducing Subconscious Neuromuscular Tension in the form of a neck wrap.
Figure 3B:
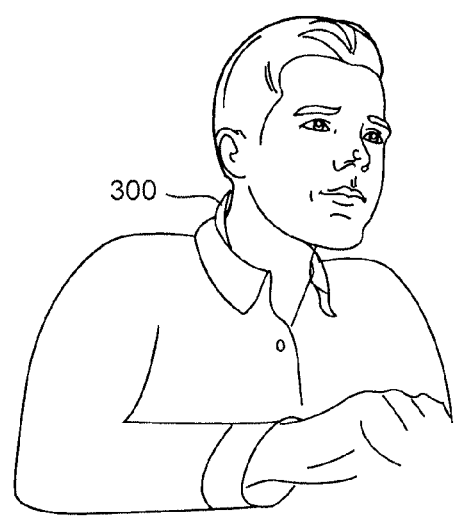
Figure 3C:
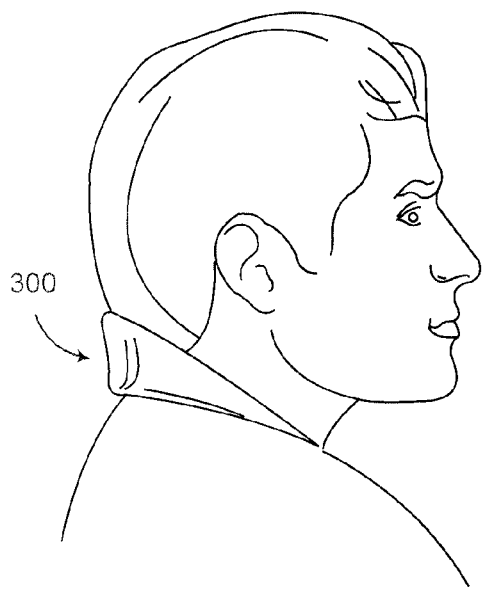
Figure 3D:
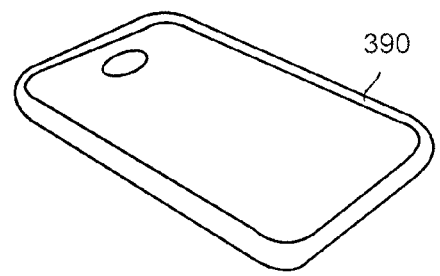
Figure 4A:
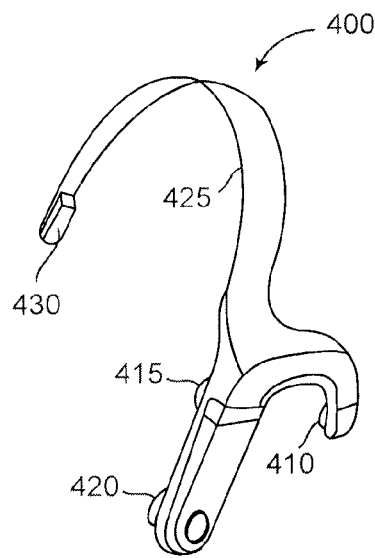
FIGS. 4a-4d show another embodiment of a System For Reducing Subconscious Neuromuscular Tension in the form of a headset.
Figure 4B:
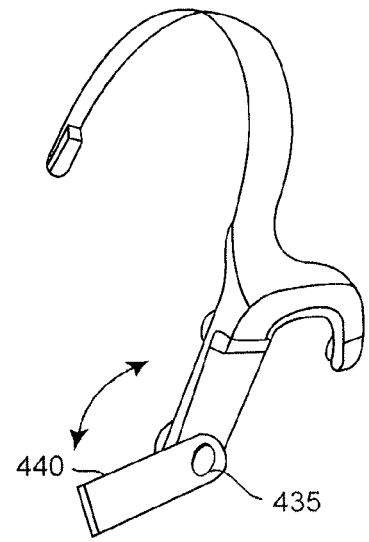
Figure 4C:
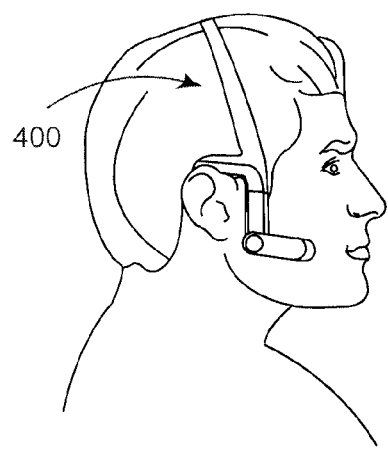
Figure 4D:
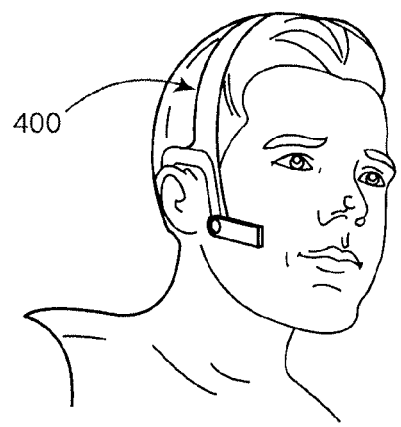
Figure 5A:
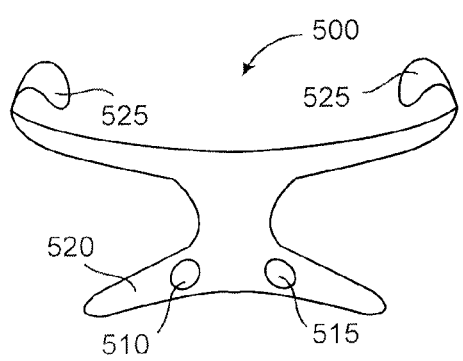
FIGS. 5a-5e show another embodiment of a System For Reducing Subconscious Neuromuscular Tension in the form of a flexible headset.
Figure 5B:
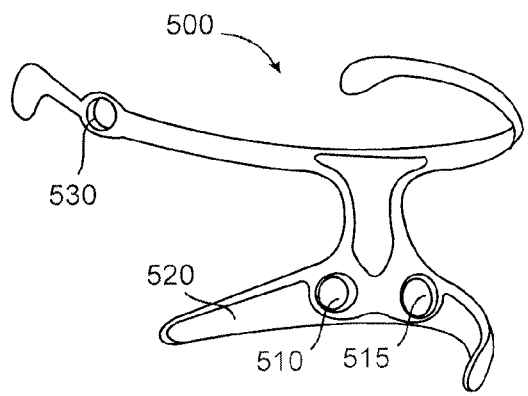
Figure 5C:
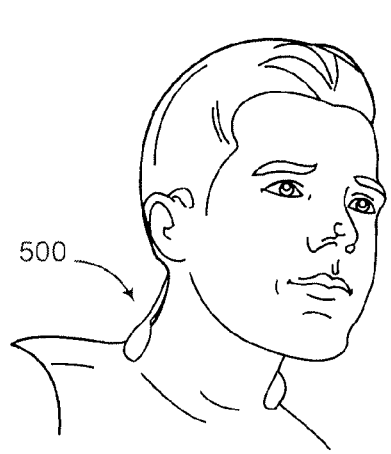
Figure 5D:
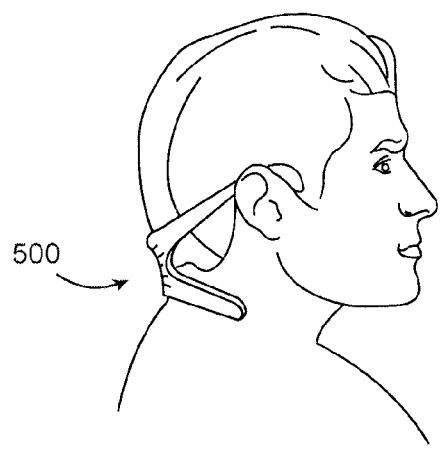
Figure 5E:
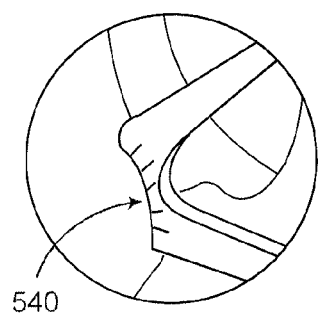
Figure 6A:
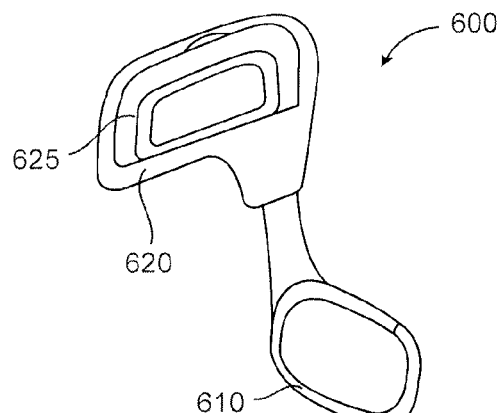
FIGS. 6a-6d show another embodiment of a System For Reducing Subconscious Neuromuscular Tension in the form of a hat clip.
Figure 6B:
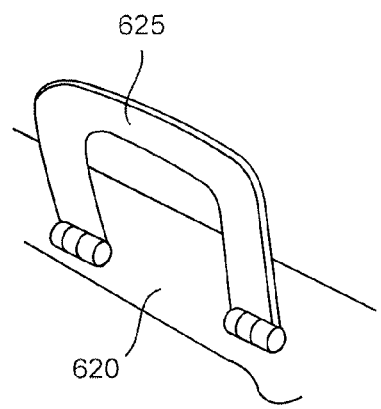
Figure 6C:
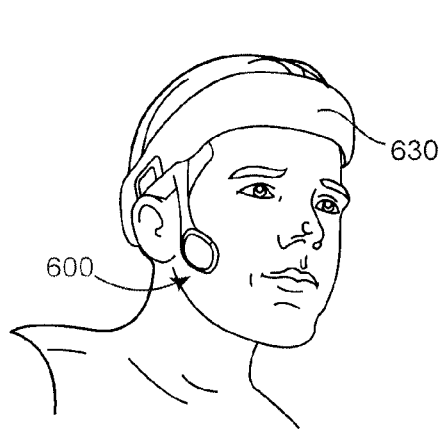
Figure 6D:
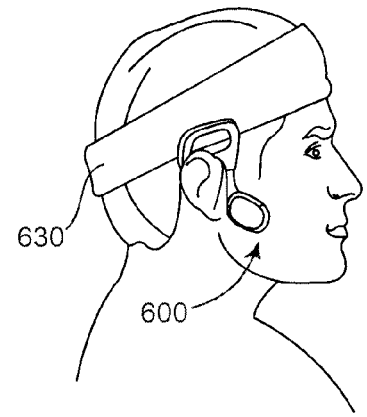
Figure 9A:
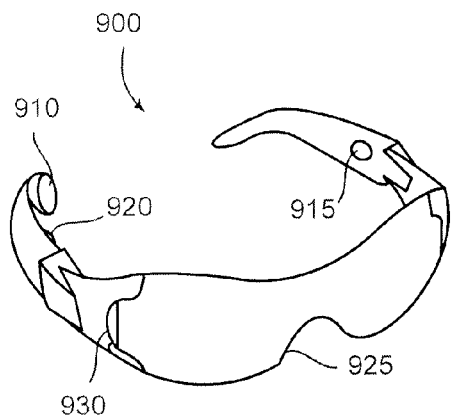
FIGS. 9a-9d shows another embodiment of a System For Reducing Subconscious Neuromuscular Tension in the form of glasses.
Figure 9B:
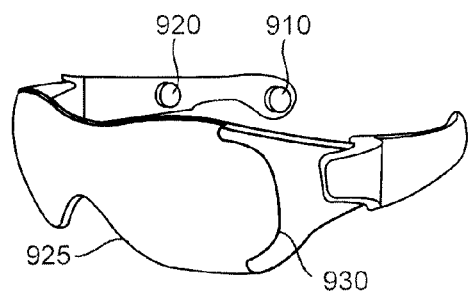
Figure 9C:
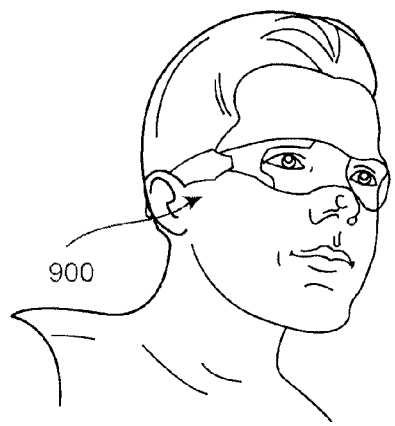
Figure 9D:
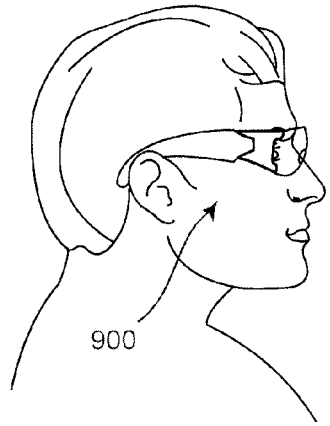

The realization that a TMJ Reduction System that is consistently used by the user is needed to combat TMJ provides for a system that is compact and largely does not interfere with the user's life. In one embodiment, the TMJ Reduction System does not provide an indication of the strength of a jaw clenching event, but instead only provides an indication of when an event occurs.

One embodiment of the TMJ Reduction System includes a "Bluetooth" earpiece looking device. The device is held on an ear using an ear loop wrapped around the back of the ear similar to one used on most Bluetooth headsets. In one alternative, the device uses a sticky adhesive around the sensors to ensure good contact with the skin. A plastic component housing is roughly between 0.5 inches×1 inch and 1 inch by 2 inches with rounded edges. Sensors are placed on an extension from the component housing extending 1 to 2 inches from the housing over the cheek and temple. The extension is approximately ¼- to ½-inch thick. It contains two sensors, a positive and a negative lead, that do not require gels for conductivity, placed at the end of the extension a small distance apart from each other. The extension is flexible allowing for optimum placement of the sensors over the masseter muscle and/or temporalis muscle. In one alternative, a ground sensor is placed away from the two main sensors, either behind the ear or elsewhere. In another alternative, a ground sensor is placed between the positive and negative sensors. In another alternative, an artificial ground is created using low impedance resistors. The casing has a power button, a sensitivity adjustment, and a battery cover. In one alternative, the TMJ Reduction System contains LED indicator light(s) and contains a volume adjustment. In one alternative, a small speaker in the ear produces a sound. In another alternative, a small motor produces a vibration to alert the wearer when they are clenching their teeth. The unit has a threshold where the user must be clenching their teeth at an adjusted intensity for a set amount of time. In one alternative, this is around three to four seconds before the device alerts the wearer. A rechargeable battery is used for the unit, for example, a lithium ion battery. In another alternative, a disposable battery is used, such as a hearing aid battery. In one embodiment, the TMJ Reduction System is integrated into another system, such as a Bluetooth headset for a mobile phone or headset for a music player (such as an MP3 Player).

In one embodiment of the method, the user puts the device on their ear and adjusts the sensor extension over their masseter or temporalis muscle. To do this a manual calibration mechanism, such as a knob, is provided. In one alternative, the device includes a calibration function. In order to calibrate, the user clenches their teeth lightly for a short period of time. The device records the signal to compare to other signals in the future to make a determination of when the user is clenching their teeth. This calibration may be stored in the device memory. Throughout the day when the user clenches their teeth, the sensors detect the EMG signals, and the amplitudes will be compared to the calibrated signal or a set standard level. If the amplitude crosses a predetermined threshold for a certain period of time, the feedback mechanism is triggered. Noise in the feedback signal from the sensors will be discarded. In one alternative, the system includes filters such as low-pass filters, etc. In another alternative, the signal is digitally processed by an IC. Feedback to the user is in the form of either a vibration or a soft noise played into the user's ear. Alternatively, the volume is adjustable. Alternatively, it may be a soft noise or the user may be able to play relaxing music or relaxation exercises. Now aware of the clenching, the user relaxes and corrects the behavior. This behavior may carry over to prevent nighttime clenching as well.

The electronics may include two alternatives, one with a calibration system, which requires a microprocessor, or one without, which only requires passive and/or active analog components to determine thresholds. In an alternative, sensitivity knobs are included that provide the user the ability to adjust the sensitivity of detection. Without the processor, the sensors detect the EMG signals. The signal goes through an amplifier to increase the amplitude. The signal goes through a low-pass filter to remove unwanted frequencies and create a cleaner signal. The signal goes through an A/D converter to create one value for the amplitude. Based on the resistors and capacitors used, if the final signal crosses a certain threshold for a certain period of time, the feedback is triggered. With the processor, the system is calibrated to allow for better precision and accuracy from person to person, as not everyone produces the exact same EMG signals. The process with the amplifier, low-pass filter, and A/D converter are the same; however, the threshold and time values are adjusted based on the calibration. The converted signal then is run back through the processor, compared to these threshold and time values, and if they are broken, the processor triggers the feedback. In one embodiment, the algorithm includes: EMG signal→amplifier, low-pass filter, A/D converter→If signal>predetermined amplitude and lasts longer than predetermined time, then biofeedback is triggered.

In one embodiment, a method includes: a user actuates calibration. The user clenches teeth during calibration. The sensor and processor sensor detect the characteristics of a clenching event. The system then monitors for an event of sufficient duration corresponding to the characteristics of a clenching event. The system notifies the user when an event is detected. Therefore, the user ceases to clench his/her teeth.

In one alternative, the system may record data related to clenching events. This information is uploaded to a computer and provided to the user so that the frequency of clenching events may be tracked. This is motivational to some users: to see the occurrence of clenching events decrease.

In one alternative, the system has two methods of operation, a record-only method and a detect-and-notify method. The record-only method is used at night and records events at night, but it does not provide feedback to the user so that the user is not awakened. The detect-and-notify method is used during the day to prevent clenching. Data from the record-only method is used to determine the progress of the therapy in respect to time periods where the user is not notified of clenching.

The masseter muscle is clearly located (but not identified in FIG. 1) on a person's cheek. The following embodiments of the Systems And Methods For Reducing Involuntary Neuromuscular Tension Including Bruxism show the apparatus with electrodes clearly placed over the masseter muscle with varying levels of pressure applied:
Head Set
Head Set 2
Hat Clip
Glasses
Bluetooth Bandage Other embodiments are also described herein. The above embodiments provide placement of the electrodes on the masseter muscle, which is preferred to placement of electrodes on the temporalis muscle.

The Systems And Methods For Reducing Involuntary Neuromuscular Tension Including Bruxism disclosed herein reduce the size of the apparatus in many areas. The following is a list outlining various elements that have been reduced in size.

The microcontroller used in the new microcontroller has no need for memory storage and does not need to control an LCD screen.

Embodiments of the current system only require a single battery. If charging is necessary, there would be a mini or micro USB connector and an IC chip (e.g. MAX1555) used to charge the battery. In some embodiments, if power consumption is low enough, the charging circuitry would be eliminated.

In some embodiments, the system is integrated in one IC (AD620 or similar) where the only external component is the Gain Resistor. The application of the AD620 is outlined below related to "Medical ECG". Furthermore, no band-pass filter is needed.

In some embodiments, a simple envelope follower with a high time constant (essentially a diode followed by a first order Low-Pass Filter) is used for purposes of event discrimination. A motor driven by a transistor (N-type BJT) controlled by a single digital output from the microcontroller is used to notify the user of a tensioning event.

In some embodiments, one instrumentation amplifier (e.g. AD620) and (e.g. AD820 or equivalent) single-supply, low power op-amps (approx. area of $31+2'16.5=64$ mm$^2$) are used as part of the detection circuit. In some embodiments, a TQFP package microcontroller has an area of only 49 mm$^2$. In some embodiments, the complexity reduction in the signal chain drives the number of parts down considerably.

One embodiment of the TMJ Reduction System includes a "headset" device. A headset device is shown in FIGS. 1a-1d. The device uses a semi rigid band wrapped around the back of the head extending from ear to ear. The housing, the electronics, feedback mechanism, and electrodes are located on one side of the unit. On the other side of the unit, the rigid band extends in order to provide enough force to keep the feedback unit secured firmly to the face. In one alternative, a form of adhesive is used to ensure good contact of the electrodes to the skin. The component housing is roughly between 0.5 inches×1 inch and 1 inch by 2 inches with rounded edges. The sensors are placed within the component housing on the side which contacts the skin. The band on this side of the unit is flexible in order to allow for sensor placement over the masseter muscle and/or temporalis muscle on different sized faces. The extension containing the sensors contains two sensors, a positive and a negative lead, that do not require gels for conductivity. The sensors are placed at a small distance apart from each other. In one alternative, a ground sensor is placed away from the two main sensors, either behind the ear, on the other side of the face, or on the back of the neck. In another alternative, a ground sensor is placed between the positive and negative sensors. In another alternative, an artificial ground is created using low impedance resistors. The casing has a power button, a sensitivity adjustment, and a mini USB port for battery charging. In one alternative, the TMJ reduction system contains LED indicator light(s) and threshold adjustment. In one alternative, a small unbalanced motor produces a vibration to alert the wearer when they are clenching their teeth. The unit has a threshold where the user must be clenching their teeth at an adjusted intensity for a predetermined amount of time. In one alternative, this is around two to four seconds before the device alerts the wearer. A rechargeable battery is used for the unit, for example, a lithium ion battery. In another alternative, a disposable battery is used, such as a hearing aid battery. In this case, a battery cover would be included on the unit. In one embodiment, the TMJ reduction system is incorporated into another system, such as a Bluetooth transmitter and receiver for mobile phones, or a headset for a music player (such as an MP3 player). Alternatively, another system is added to the TMJ reduction system.

A method for using the TMJ reduction system includes the user placing the device on their head and adjusting the device to get the sensors in contact with the skin over the masseter or temporalis muscles. The user uses a knob or other calibration system in order to adjust the sensitivity of the device. In one alternative, the device includes a calibration function. In order to calibrate, the user clenches their teeth lightly for a short period of time. The device records the signal to compare to other signals in the future to make a determination of when the user is clenching their teeth. This calibration may be stored in the device memory. In another alternative, the user will manually calibrate the device. The user will lightly clench their teeth and adjust the sensitivity to the appropriate clench intensity at which they would like to receive feedback. Throughout the day when the user clenches their teeth, the sensors detect the EMF signals; and the amplitudes will be compared to the calibrated signal or a set standard level. If the amplitude crosses a predetermined threshold for a certain period of time, the feedback mechanism is triggered. Noise in the feedback signal from the sensors will be discarded. In one alternative, the system includes filters such as low-pass filters, etc. In another alternative, an IC digitally processes the signal. In another alternative, the signal is input into an algorithm that determines whether or not to trigger the feedback. Feedback to the user is in the form of a vibration. Now aware of the clenching, the user relaxes and corrects the behavior. This behavior may carry over to prevent nighttime clenching as well.

The basic design includes a number of configurations that allow for correct placement of sensors and comfort and fit of the device for the user. FIGS. 1a-1d show one embodiment of a System For Reducing Subconscious Neuromuscular Tension in the form of a headset 100. Headset 100 includes first and second electrodes 110, 115 for sensing muscular tension and creating an electrical signal. The components of the circuitry that receive and process signals is described in detail below. Headset 100 further includes a ground 120 for providing a reference to electrodes 110, 115. In this embodiment, the headset 100 further includes a speaker 135 located in headset body 130. The speaker 135 or vibration unit may be used for notifying the user when a clenching event is occurring. Headset 100 further includes an ear rest 125, a frame 140, and flexible end 145 for softening the pressure applied against the side of the user's head. FIGS. 1c and 1d further show the fit and engagement of headset 100 on the head of a user. The design of the headset body 130 that houses first and second electrodes 110, 115 allows for these electrodes to be placed over the masseter, while still providing a high degree of comfort to the user. The placement and extension of a body piece allow placement of first and second electrodes 110, 115 directly over the masseter.

FIGS. 2a-2d show another embodiment of a System For Reducing Subconscious Neuromuscular Tension in the form of a croakie 200. In this arrangement, croakie 200 is designed to fit on glasses 250. It includes croakie tubes 210, with open ends 215 for fitting on the arms of glasses 250. Additionally, openings 212 allow for the tips of the arms of glasses 250 to stick out. Croakie 200 includes fitted section 220, designed to fit to the user's neck. In some embodiments, fitted section 220 may include adhesive in order to more closely fit to the user's neck. Electrodes 220, 225 are also shown, as well as ground 235. The tensing of muscles in the neck is directly monitored in this embodiment, as opposed to the masseter muscle directly. This design attaches to glasses by connecting to the arms of the glasses and wrapping around the back of the wearers neck. The positive, negative, and ground sensors are housed in a casing that rests on the back of the user's neck. One alternative uses a sticky adhesive around the sensors to ensure good contact with the skin. The plastic housing is located behind the neck and is roughly 0.5 inches×1 inch and 1 inch×2 inches with rounded edges. It contains two sensors, a positive and a negative lead, that do not require gels for conductivity. In one alternative, a third ground electrode is placed between the positive and negative electrodes. In another alternative, the ground sensor is placed away from the two main sensors, either behind the ear or another part of the neck. In yet another alternative, an artificial ground is created using low impedance resistors. The casing has a power button, a sensitivity adjustment, and a mini USB port for charging the battery. In one alternative, the system contains LED indicator light(s). In another alternative, a small unbalanced motor produces a vibration to alert the wearer when they are clenching their teeth or experiencing stress. The unit has a threshold where the user must be clenching their teeth at an adjusted intensity for a certain amount of time. In one alternative, this is around two to four seconds before the device alerts the wearer. A rechargeable battery is used for the unit, for example, a lithium ion battery. In another alternative, a disposable battery is used, such as a hearing aid battery. In this case, a battery door will be included.

FIGS. 3a-3d show another embodiment of a System For Reducing Subconscious Neuromuscular Tension in the form of a neck wrap 300. Neckwrap 300 is very similar to croakie 200 in many aspects. It includes a device body, two electrodes, 325, 315, a ground 320, wrap around section 310, and in some alternatives adhesive sections. In this embodiment, a portable electronic device 350 is shown. This device 350 receives signals from the neckwrap 300 when a tension event is detected and displays a message to the user to calm down, or provides other physical (vibration), visual, or audio cues that an event is occurring. This design is housed in an ergonomic casing that wraps around the base of the neck and sits just below the collar of a shirt. The positive, negative, and ground sensors are housed in the casing so that they are placed at the back of the neck. One alternative uses a sticky adhesive around the sensors to ensure good contact with the skin. The plastic housing extends from just above the collarbone on one side of the body, around the back of the neck, to just above the collarbone on the other side of the body. The plastic housing is roughly 0.5 inches in thickness, roughly 1 inch wide, and roughly 16 inches from end to end. The ends of the unit, located above the collarbones, are flexible to allow comfortable placement. The unit contains two sensors, a positive and a negative lead, that do not require gels for conductivity. In one alternative, a third ground electrode is placed between the positive and negative electrodes. In another alternative, the ground sensor is placed away from the two main sensors, either another part of the neck or near the collarbone. In another alternative, an artificial ground is created using low impedance resistors. The casing has a power button, a sensitivity adjustment, and a mini USB port for charging the battery. In one alternative, the system contains LED indicator light(s). In another alternative, a small unbalanced motor produces a vibration to alert the wearer when they are clenching their teeth or tightening other muscles. The unit has a threshold where the user must be clenching their teeth at an adjusted intensity for a set amount of time. In one alternative, this is around two to four seconds before the device alerts the wearer. A rechargeable battery is used for the unit, for example, a lithium ion battery. In another alternative, a disposable battery is used, such as a hearing aid battery. In this case, a battery door will be included.

FIGS. 4a-4d show another embodiment of a System For Reducing Subconscious Neuromuscular Tension in the form of a headset 400. Headset 400 includes ground 410, electrodes 415, 420, frame 425, and pad 430. Additionally, this embodiment includes a microphone 440 that extends in a rotational fashion using pivot 435. Although not shown in the figures, in alternatives, this embodiment may include a speaker or headphone that is insertable in the user's ear. In this case, the headset provides the dual function of being a microphone and headset, while at the same time providing for the detection of tension events.

FIGS. 5a-5d show another embodiment of a System For Reducing Subconscious Neuromuscular Tension in the form of a flexible headwrap 500. Headwrap 500 is very similar to croakie 200 in many aspects. It includes a device body, two electrodes, 510, 515, a ground 530, adhesive section 520, and ear supports 525.

FIGS. 6a-6d show another embodiment of a System For Reducing Subconscious Neuromuscular Tension in the form of a hat clip 600. Hat clip 600 includes a clip portion 620 with a clip 625. Clip 625 can be used to attach the hat clip 600 to a head band 630 or hat. The sensor array, similar to that described in previous embodiments, is housed in body 610.

FIGS. 7a-7e show another embodiment of a System For Reducing Subconscious Neuromuscular Tension in the form of a croakie 700. This embodiment differs from croakie 200 in that croakie 700 is placed at a much higher position on the head of the user, and the band 730 is elastomeric. Instead of the diodes being on the rear portion of the croakie, the electrodes 725 are on either side of the user's head. Ground 720 is located behind the ear of the user. Housing 710 contains the associated electronics for the system.

FIGS. 8a-8d show another embodiment of a System For Reducing Subconscious Neuromuscular Tension in the form of glasses 800. Glasses 800 include electrodes 815, 820 which are oriented to press on the masseter muscle directly and ground 810. They include a frame 825 and LED visual indicator 830. LED visual indicator 830 activates when a muscle tensioning event is occurring.

FIGS. 9a-9d show another embodiment of a System For Reducing Subconscious Neuromuscular Tension in the form of glasses 900. In this embodiment, electrodes 915, 920 press into the sides of the head of the user. Glasses 900 include frame 925. ground 910, and visual indicator 930.

Figure 10A:
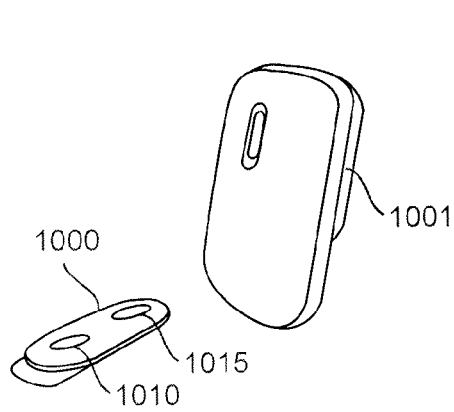
FIGS. 10a-10d show another embodiment of a System For Reducing Subconscious Neuromuscular Tension in the form of a Bluetooth bandage.
Figure 10B:
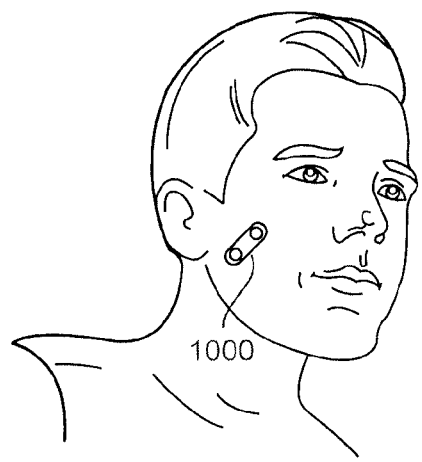
Figure 10C:
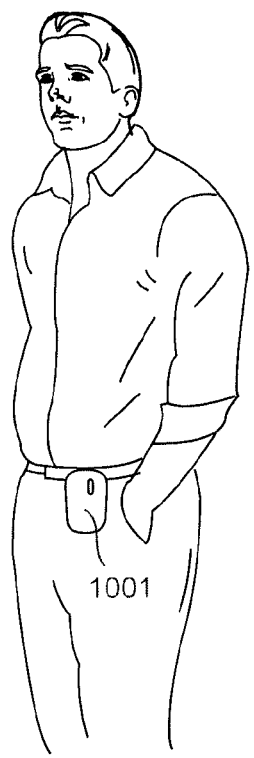
Figure 10D:
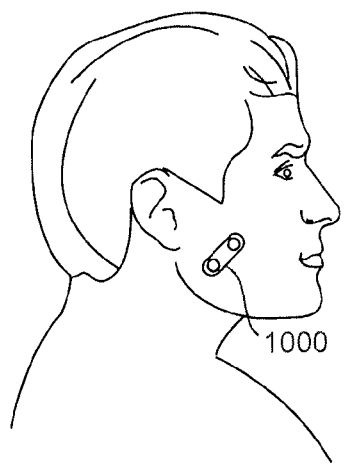

FIGS. 10a-10d show another embodiment of a System For Reducing Subconscious Neuromuscular Tension in the form of a Bluetooth bandage 1000. Bandage 1000 has an adhesive so that it may stick to the face of the user. It includes electrodes 1010, 1015 and may be placed directly over the masseter. The bandage 1000 includes Bluetooth transmission circuits and sends a signal to unit 1001, which acts to process the incoming signal and deliver indicators to the user when a contraction event is occurring. In FIG. 10a, this device is shown as an independent unit. In alternatives, unit 1001 may be a smart phone, PDA, or other device capable of receiving a Bluetooth signal.

Figure 11A:
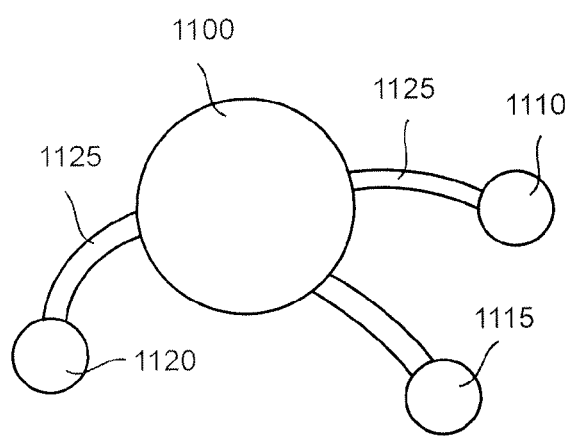
FIGS. 11a-11c show another embodiment of a System For Reducing Subconscious Neuromuscular Tension in the form of a headset attachment.
Figure 11B:
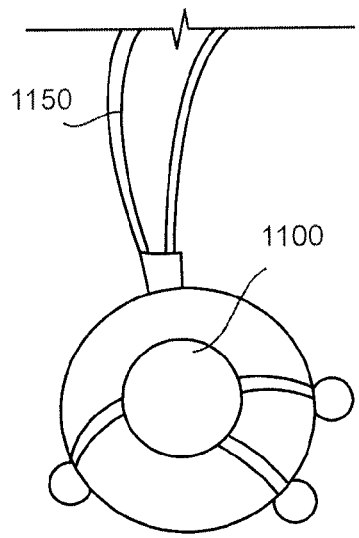
Figure 11C:
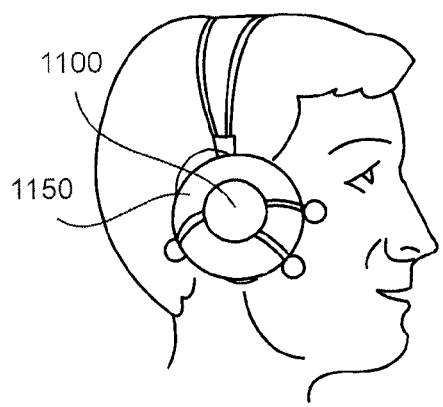

FIGS. 11a-11c show another embodiment of a System For Reducing Subconscious Neuromuscular Tension in the form of a headset attachment 1100. Headset attachment 1100 fits over a headset 1150 and includes electrodes 1110, 1115 and ground 1120, as well as connection arms 1125. This embodiment is designed to fit over headset 1150. In some embodiments, connection arms 1125 are flexible and hold the position they are flexed into. Electrode 1110 is for the anterior, electrode 115 is for the masseter muscle, and sensor 1120 servers as a reference electrode.

Figure 12A:
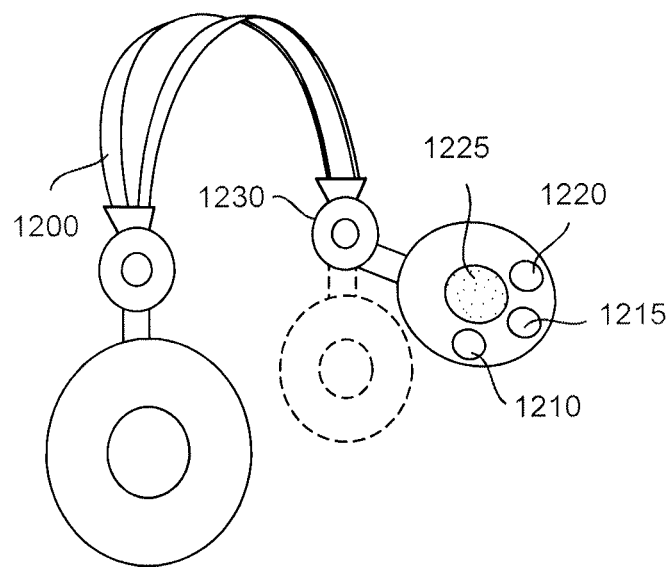
FIGS. 12a and 12b show another embodiment of a System For Reducing Subconscious Neuromuscular Tension in the form of a swivel headset.
Figure 12B:
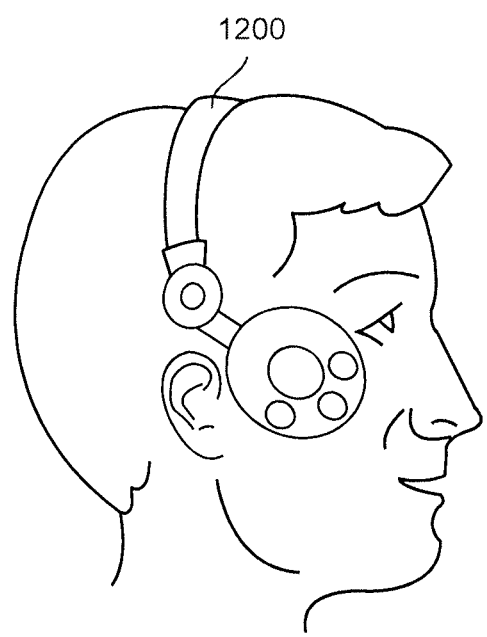

FIGS. 12a and 12b show another embodiment of a System For Reducing Subconscious Neuromuscular Tension in the form of a swivel headset 1220. Swivel headset 1220 includes a swivel hinge 1230, sensors 1220, 1215, 1210, and speaker 1225. The swivel hinge 1230 allows the headset to be positioned either over the ear of the user to sense the masseter muscle or rotated forward to sense the temporalis and/or procerus muscle.

Figure 13A:
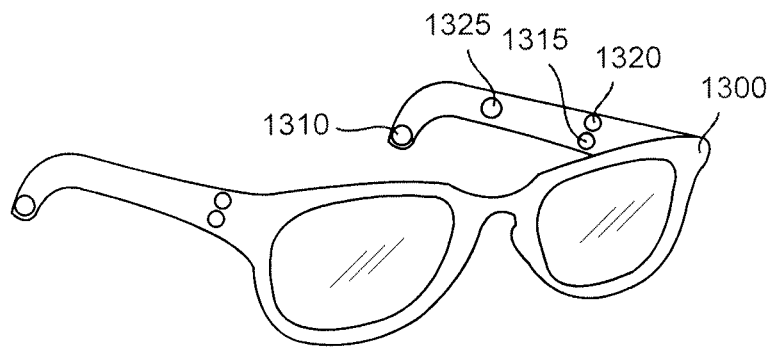
FIGS. 13a and 13b show another embodiment of a System For Reducing Subconscious Neuromuscular Tension in the form of glasses.
Figure 13B:
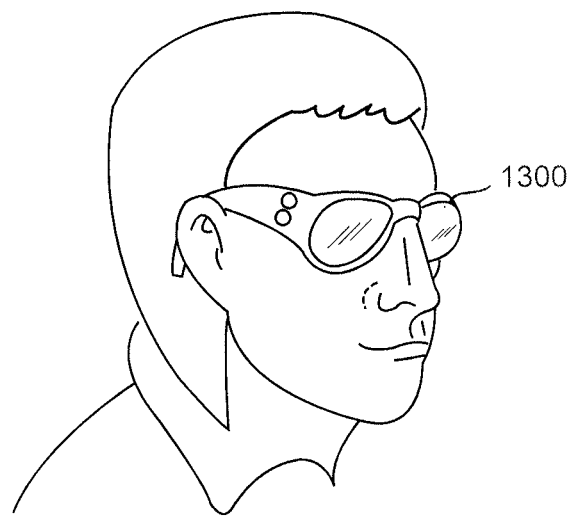

FIGS. 13a and 13b show another embodiment of a System For Reducing Subconscious Neuromuscular Tension in the form of glasses 1300. Glasses 1300 include a reference electrode 1310, sensor electrodes 1315, 1320, and speaker or vibrator/oscillator 135. In this case, sensor electrodes 1315, 1320 are positioned over the temporalis muscle or the Frontalis or procerus muscles over the forehead (different configuration than shown).

Figure 14A:
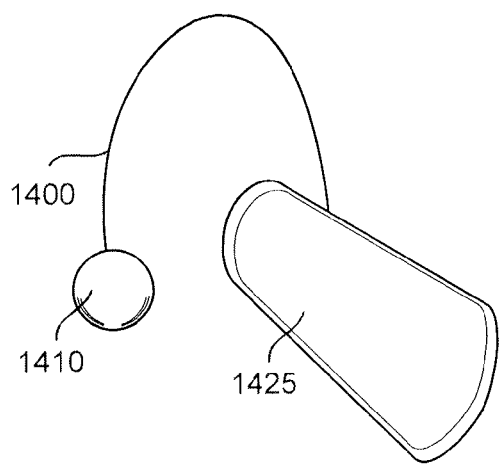
FIGS. 14a-14c show another embodiment of a System For Reducing Subconscious Neuromuscular Tension in the form of a Bluetooth headset.
Figure 14B:
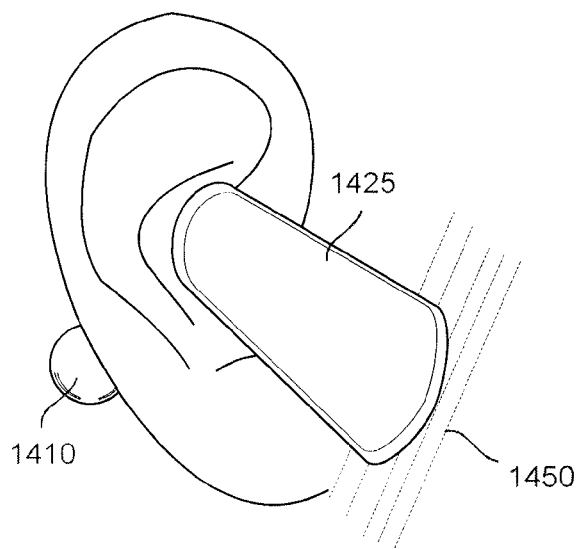
Figure 14C:
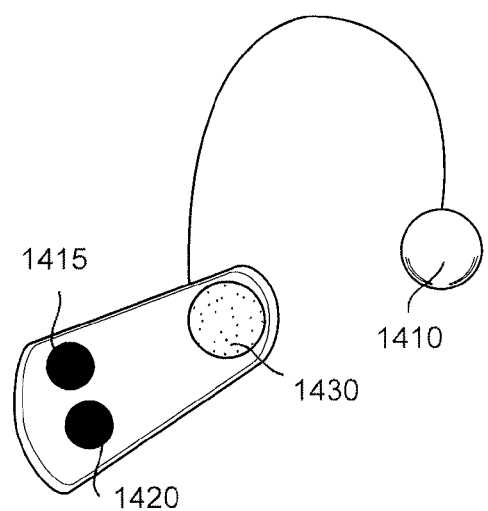

FIGS. 14a-14c show another embodiment of a System For Reducing Subconscious Neuromuscular Tension in the form of a Bluetooth headset 1400. Bluetooth headset 1400 includes sensors 1415, 1420, reference 1410, and speaker 1430. It is configured to fit over masseter muscle 1450. This headset may include the functions of a traditional Bluetooth headset that is used with a mobile phone. In this configuration, the Bluetooth headset has a larger width than a typical Bluetooth headset due to the vertical arrangement of the sensors. This provides for enhanced sensing of the masseter muscle.

Figure 15A:
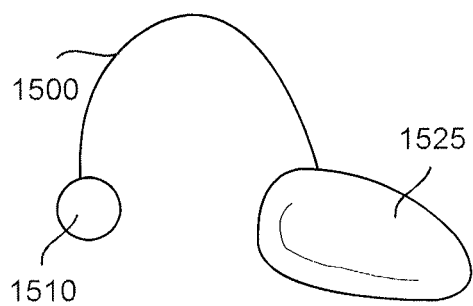
FIGS. 15a-15c show another embodiment of a System For Reducing Subconscious Neuromuscular Tension in the form of a Bluetooth headset.
Figure 15B:
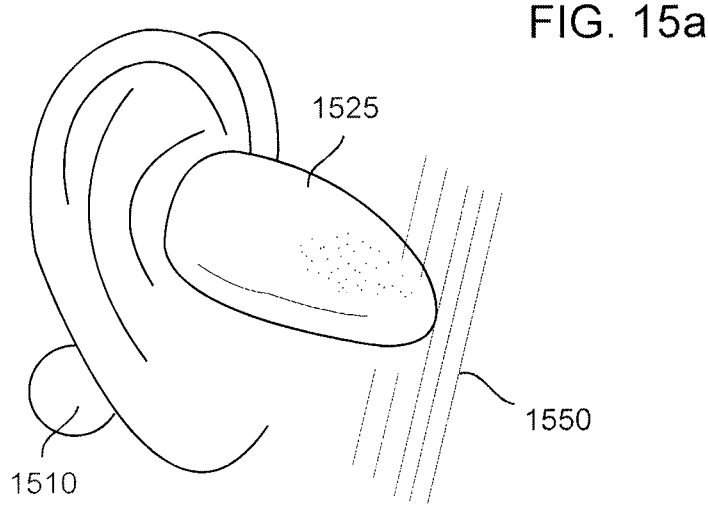
Figure 15C:
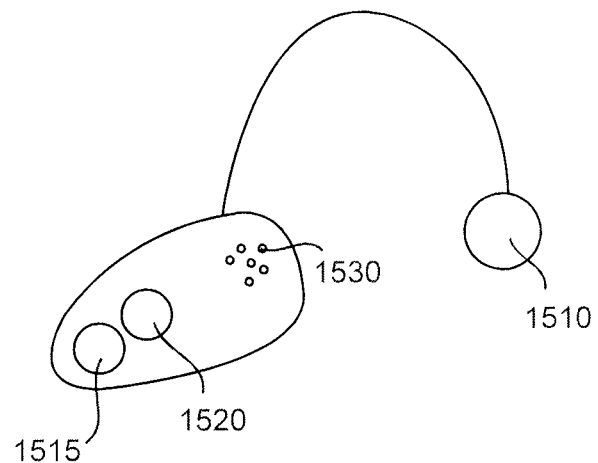

In contrast, FIGS. 15a-15c show another embodiment of a System For Reducing Subconscious Neuromuscular Tension in the form of a Bluetooth headset 1500. Bluetooth headset 1500 includes sensor 1515, 1520, reference 1510, and speaker 1530. It is configured to fit over masseter muscle 1550. This headset may include the functions of a traditional Bluetooth headset that is used with a mobile phone. In this configuration, the Bluetooth headset has a narrow width like a typical Bluetooth headset does due to the horizontal arrangement of the sensors.

Figure 16A:
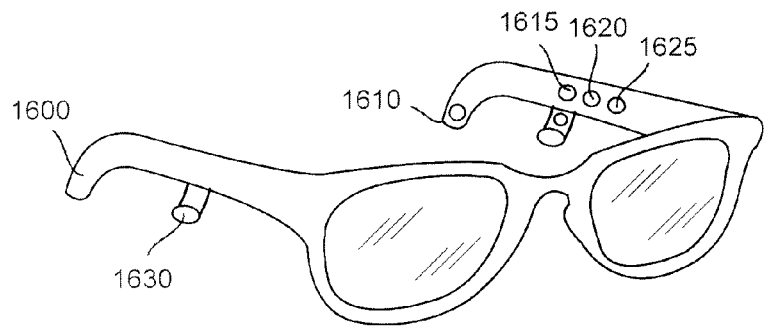
FIGS. 16a-16d show another embodiment of a System For Reducing Subconscious Neuromuscular Tension in the form of glasses.
Figure 16B:
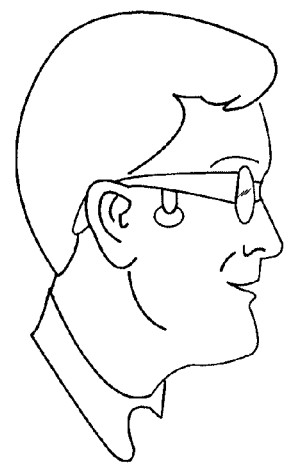
Figure 16C:
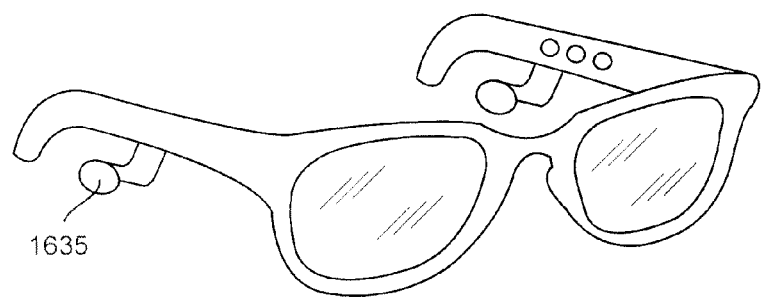

FIGS. 16a-16c show another embodiment of a System For Reducing Subconscious Neuromuscular Tension in the form of glasses 1600. Glasses 1600 include sensors 1615, 1620, reference 1610, and bone oscillator 1630. FIG. 16c shows an alternative that provides for a speaker 1635 that fits into an ear of the user. This configuration provides for monitoring of the temporalis muscle with speakers, or an oscillator transmitting a tone or music into the zygomatic arch.

Figure 16D:
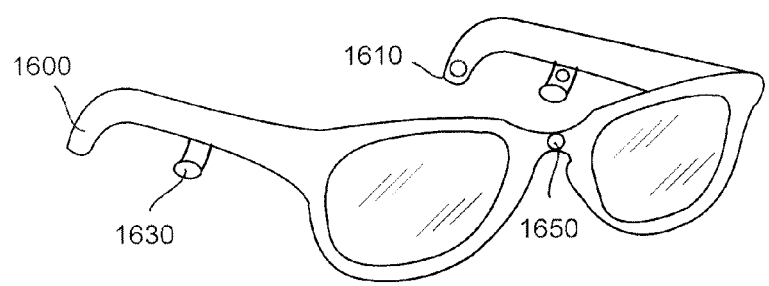

FIG. 16d shows an alternative but similar embodiment to FIGS. 16a-16c. In this embodiment, positive and negative electrodes 1630 are located in the arm that drops down. In one embodiment there would be a positive and negative electrode on each side of the head, and in another embodiment the positive electrode would be on one side of the head, and the negative electrode would be on the other. Another embodiment for FIG. 16d have the ground electrode either where 1610 is located, or have the ground be in the bridge 1650 where it contacts the nose.

Figure 17A:
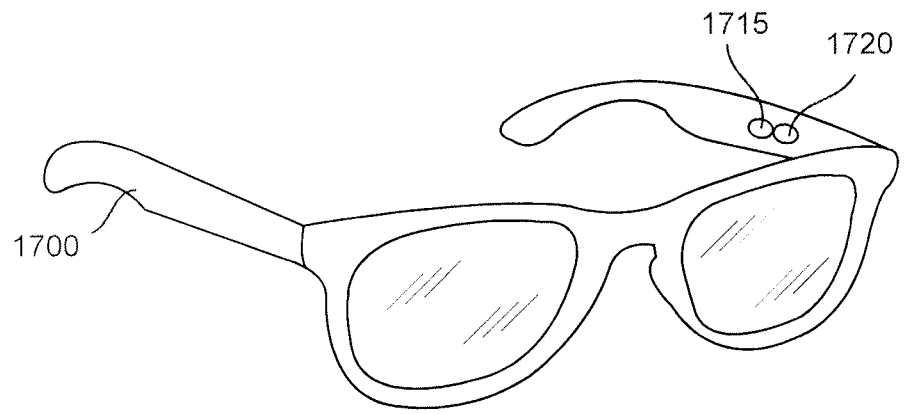
FIGS. 17a and 17b show another embodiment of a System For Reducing Subconscious Neuromuscular Tension in the form of glasses.
Figure 17B:
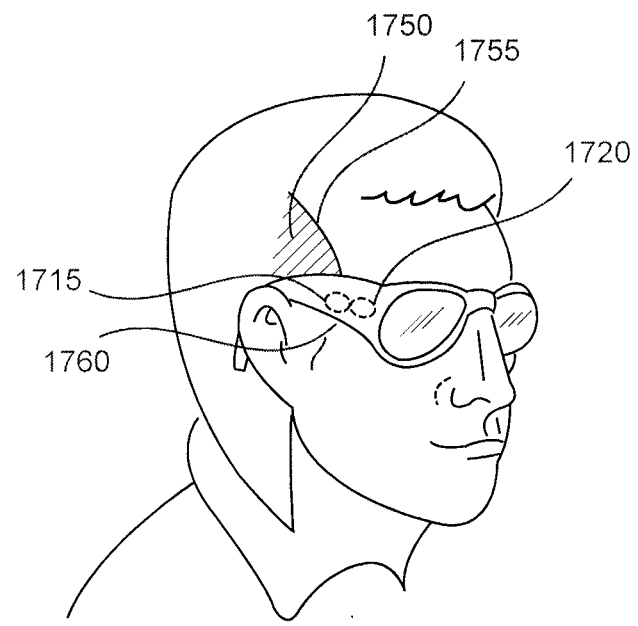

FIGS. 17a and 17b show another embodiment of a System For Reducing Subconscious Neuromuscular Tension in the form of glasses 1700. Glasses 1700 include a vibrator 1715 and a sensor 1720. FIG. 17b shows the fit of the glasses, directly over the temporalis muscle 1750 near the temporalis ridge 1755. The vibrator 1715 rests directly on the zygomatic arch 1760.

Figure 18A:
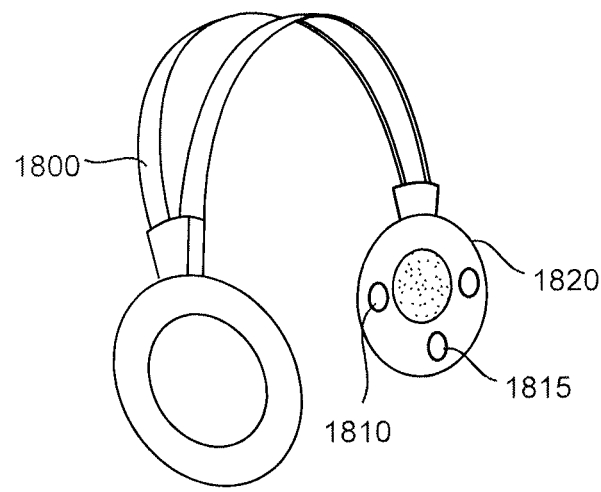
FIGS. 18a and 18b show another embodiment of a System For Reducing Subconscious Neuromuscular Tension in the form of a headset.
Figure 18B:
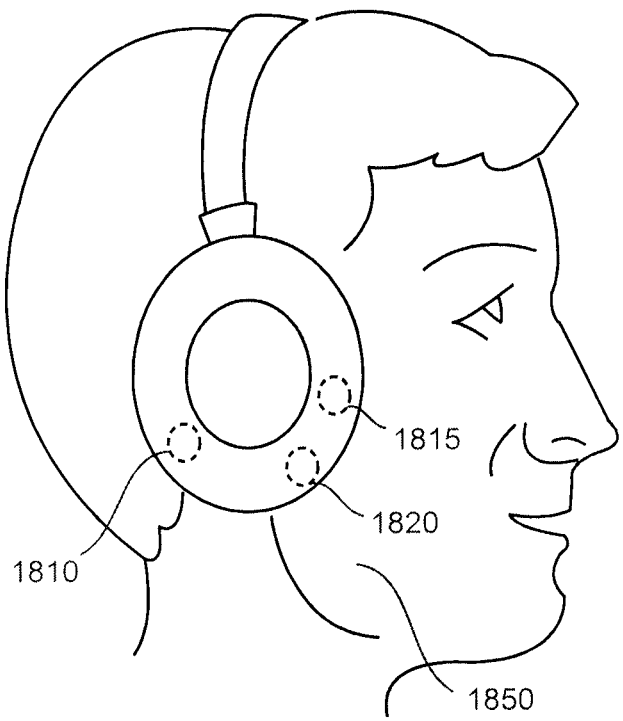

FIGS. 18a and 18b show another embodiment of a System For Reducing Subconscious Neuromuscular Tension in the form of a headset 1800. Headset 1800 includes sensors 1815, 1820 and reference 1810. In this embodiment, the sensors are incorporated into the pads of the ear piece. The sensors sit on the masseter muscle.

Figure 20:
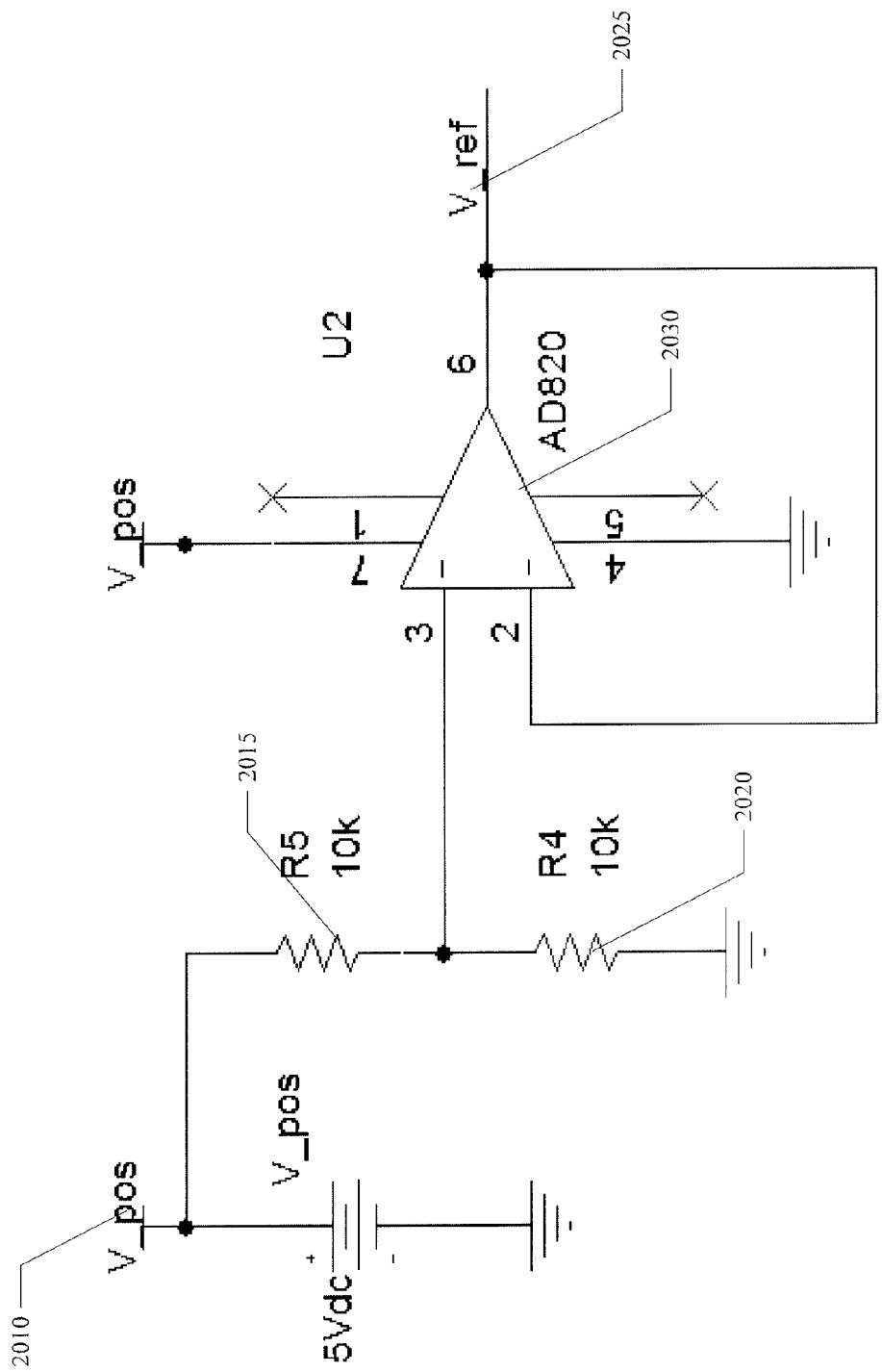
FIG. 20 shows an embodiment of a voltage divider and buffer for use in a System For Reducing Subconscious Neuromuscular Tension.

FIG. 20a shows an embodiment of a voltage divider for use in a System For Reducing Subconscious Neuromuscular Tension. The voltage supplied to the circuit by a battery, $V_{out}$ 2025, is regulated at 5V (or 3.3V) and used as the positive voltage supply (V+) to all active components in the circuit. The negative voltage supply is actually ground (GND); thus, the circuitry is referred to as single-supply rail. Since low signal voltages referenced to ground would be too low to positively bias a diode (~0.7V), the entire signal chain is referenced at a "virtual ground" ($V_{\_REF}$) of approximately half the positive supply, 2.5V (or 1.65V). This is accomplished using a voltage divider, shown in FIG. 20a, where the resistance of resistor R1 2015 is equal to the resistance of resistor R2 2020. Voltage is supplied by the battery, $V_{in}$ 2010, and regulated by the circuit shown yielding a regulated out voltage, $V_{out}$ 2025. The divider is followed by a unity gain voltage buffer shown in FIG. 1b, so input resistances of other components cannot affect the reference voltage, $V_{\_REF}$. The unity gain voltage buffer receives a voltage provided by the voltage divider of FIG. 20, $V_{in}$ 2010. Operational amplifier 2030 receives this input at the non-inverting port and is controlled by the negative feedback loop connected to the inverting port. This yields an amplified output voltage, $V_{out}$ 2025.

Figure 19A:
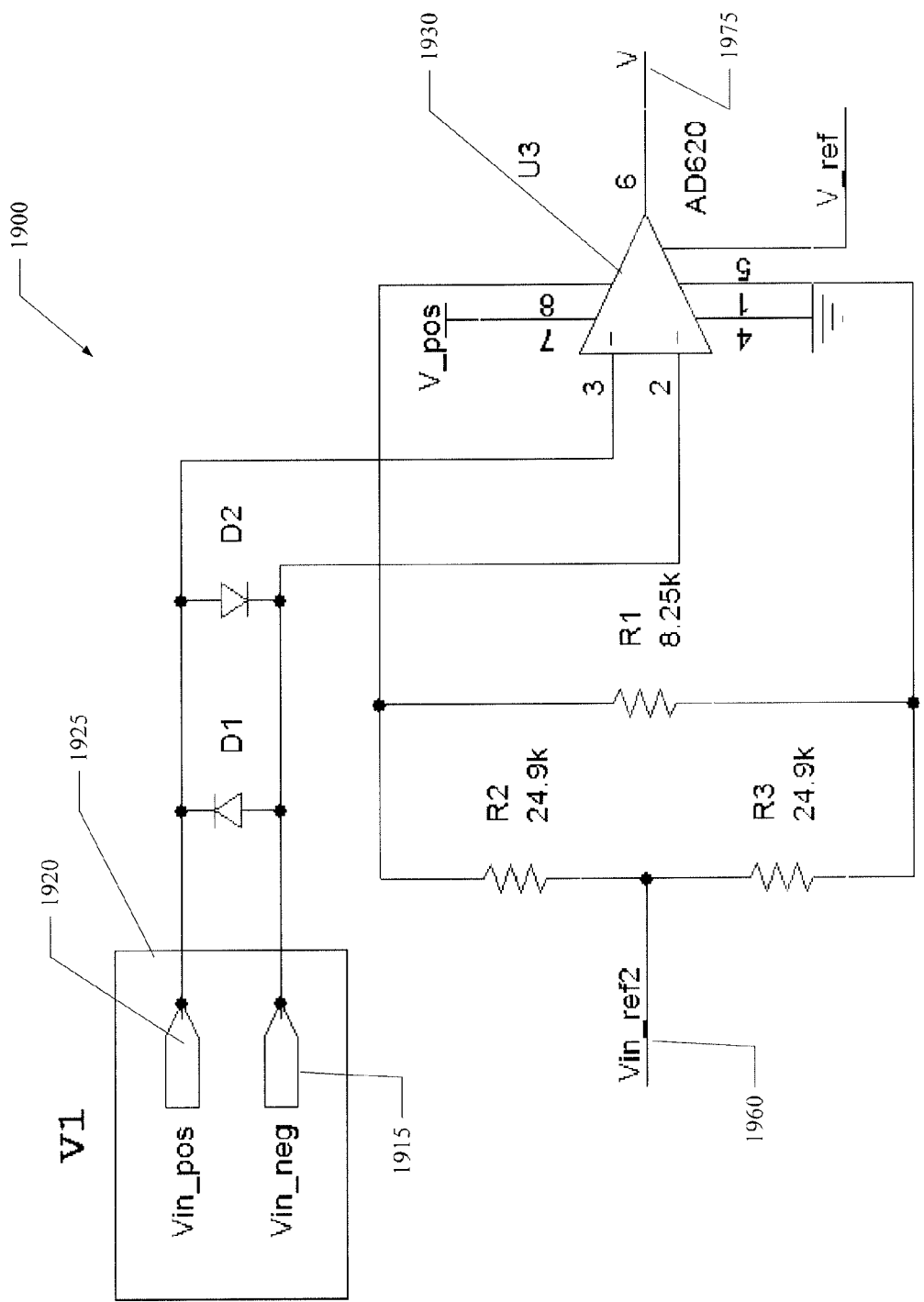
FIGS. 19a and 19b show an embodiment of a Medical ECG Monitor Circuit for use in a System For Reducing Subconscious Neuromuscular Tension.
Figure 19B:
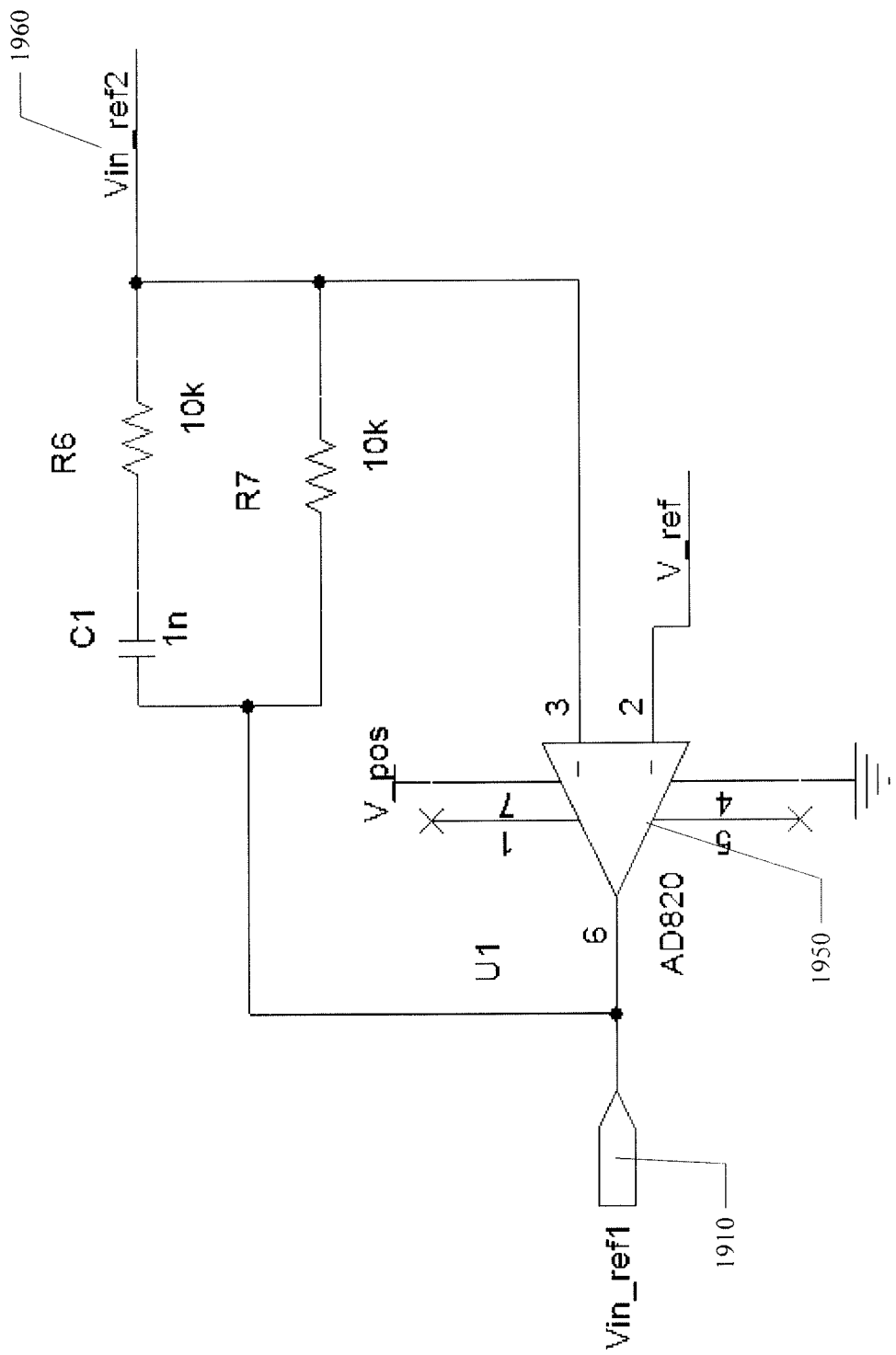

FIG. 19 shows an embodiment of a Medical ECG Monitor Circuit 1900 for use in a System For Reducing Subconscious Neuromuscular Tension. Device wall 1925 is symbolic of the device case in which the device is implemented. The input signal (V1) is the differential voltage between two of the three electrodes, 1910, 1915, 1920 placed on the user's body. These two electrodes, 1915, 1920, ideally are placed on the masseter muscle but may also be placed on the temporalis muscle in alternate embodiments of the apparatus. The third electrode 1910 deliberately is placed on a part of the body with fewer muscle fibers (e.g., behind the user's ear) and is used as a body reference signal ($BDY_{\_REF}$). The signal V1 then is applied at the differential inputs to a low-power, single supply rail instrumentation amplifier as shown as AD620 ECG 1930. The REF signal 1910 is applied at the output of a low-power, single supply rail op-amp 1950 that varies the effective gain resistance of the instrumentation amplifier. A conditioned reference 1960 signal is output. The DC bias provided by $V_{\_REF}$ is desired in achieving output 1975. A high-pass filter would eliminate this desired effect, and secondary gain would be detrimental given the amplification of $V_{\_REF}$ that would inherently result.

Figure 21B:
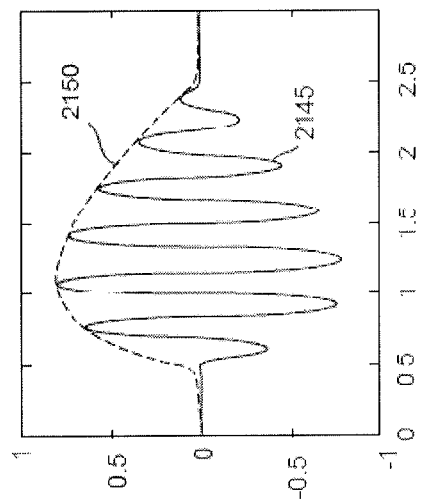
Figure 21A:
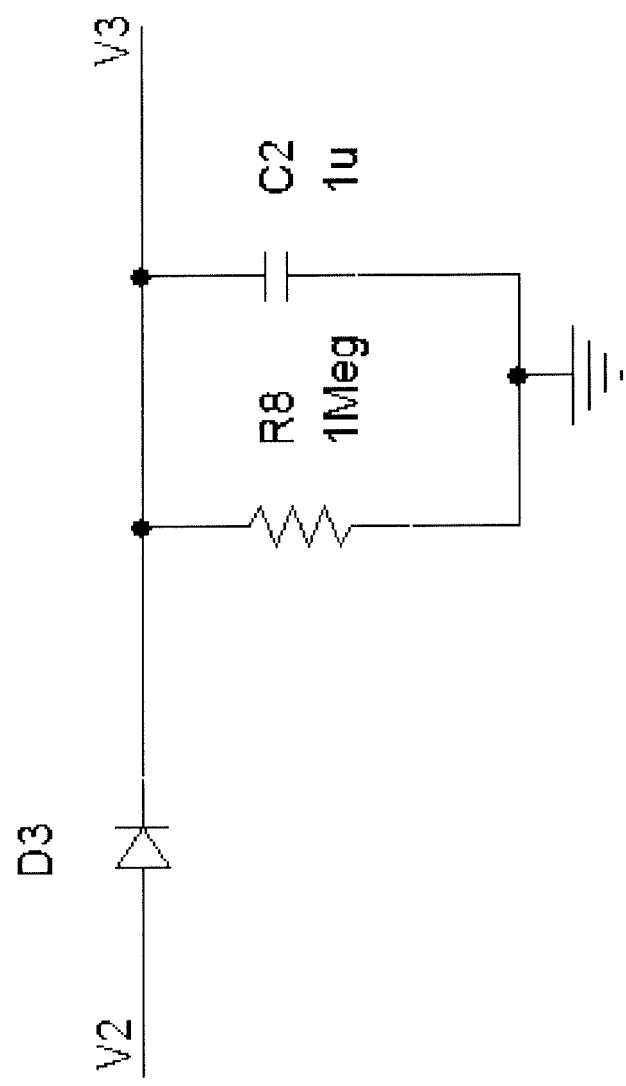
FIG. 21a shows a schematic of an envelope follower/detector for use in a System For Reducing Subconscious Neuromuscular Tension.

The signal V2 is a signal that has a DC bias of approximately $V_{\_REF}$, a low-amplitude high frequency component (noise) and a high amplitude medium frequency component that occurs when the user is "bruxing." "Bruxing" is defined as clenching, grinding, or gritting of the user's teeth, which results in a low differential voltage across the electrodes attached to the muscle. The amplified result has a lower frequency component than the noise, but can effectively be modeled as noise at a higher amplitude than the "noise floor" (~100-500 mV compared to <10 mV). The signal V2 then is applied to a simple, passive "envelope follower/detector," shown in FIG. 21a, resulting in signal V3. If the input voltage V2 is greater than a "diode drop" (~0.7V) above the output voltage, the output voltage rises to V2-0.7 Volts. The rise time of signal V3 is determined by the parallel combination of the diode's "on" resistance, rd, the resistor R, and the capacitor C. This rise time primarily is determined by rd//ZC as opposed to the fall time which is solely determined by R//ZC. The fall time deliberately is calculated to be long so any detection of "bruxing" will result in a signal V3 that stays high much longer than the actual event of "bruxing" that has been modeled as noise. The signal V3 then is input to the microcontroller's built-in analog-to-digital converter. FIG. 21b shows a graph of input voltage 2145 and output voltage 2150.

Figure 22A:
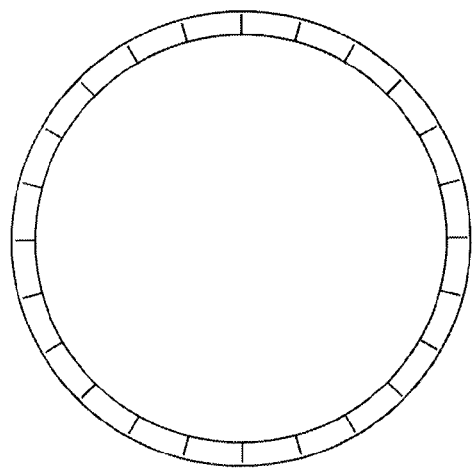
FIGS. 22a and 22b show schematics of a ring buffer for use in a System For Reducing Subconscious Neuromuscular Tension.
Figure 22B:
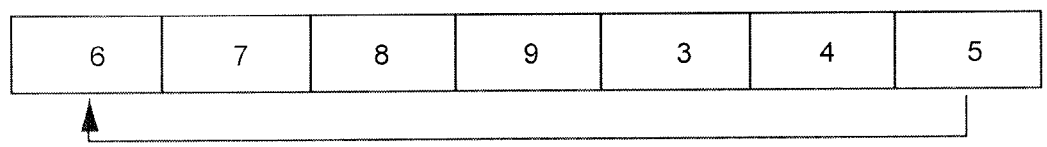

The microcontroller's analog-to-digital converter converts the analog input of signal V3 to an N-bit digital signal. The firmware installed on the microcontroller then uses a technique known as ring buffering (shown in FIGS. 22a and 22b) to average the N-bit representation of V3, resulting in signal V4. The signal V3 simultaneously is averaged by a much larger ring buffer that results in the baseline voltage signal, $V_{BL}$. This larger ring buffer is due to the inherent "drift" of the signal above or below $V_{\_REF}$. A static baseline voltage would produce false positives or false negatives for bruxing due to drift, while the dynamic baseline voltage eliminates these errors.

Figure 23:
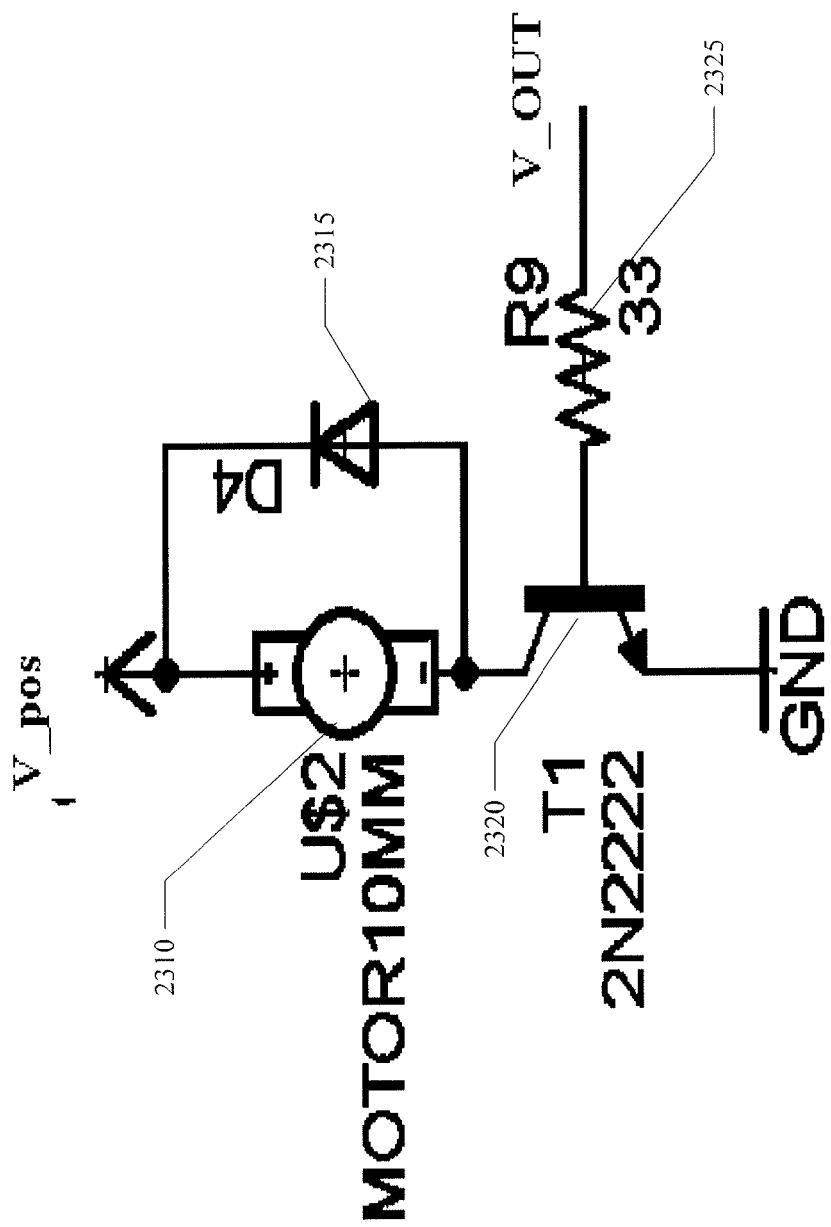
FIG. 23 shows an exemplary vibration motor control for use in a System For Reducing Subconscious Neuromuscular Tension.

After using a ring buffer to average the signal (resulting in V4), a variable (manual or pre-calibrated) threshold voltage, $V_{TH}$, is subtracted from V4 and compared to the dynamic baseline voltage, $V_{BL}$. If this value is greater than the baseline for a pre-determined amount of time (e.g., two to four seconds), the microcontroller sets the output voltage, $V_{OUT}$, to a HIGH (5V) value for a pre-determined amount of time that is long enough for the user to cognitively cease "bruxing" activity. The output $V_{OUT}$ is digital and can have a value of LOW (0V) or HIGH (5V). A 'HIGH' $V_{OUT}$ will turn on an N-type transistor that drives the bio-feedback output (e.g., a vibration motor for one embodiment). FIG. 23 shows a circuit driving a motor 2310 that uses an output 'LOW' voltage to turn on the motor and includes resistor 2325, transistor 2320, and diode 2315. In the event of vibration (either constant or pulsing) as a result of a bruxing event, the user will cease bruxing and the value of (V4-$V_{TH}$) will drop below $V_{BL}$, and the next loop through the microcontroller's logic will set the value of $V_{OUT}$ to 'LOW' after the pre-determined time of vibration feedback. If the user continues to be bruxing, the logic will keep the motor turned on. In alternate embodiments of bio-feedback, the continued user bruxing will result in a higher amplitude of vibration implemented using a digital output that is pulse-width modulated (PWM).

Figure 24A:
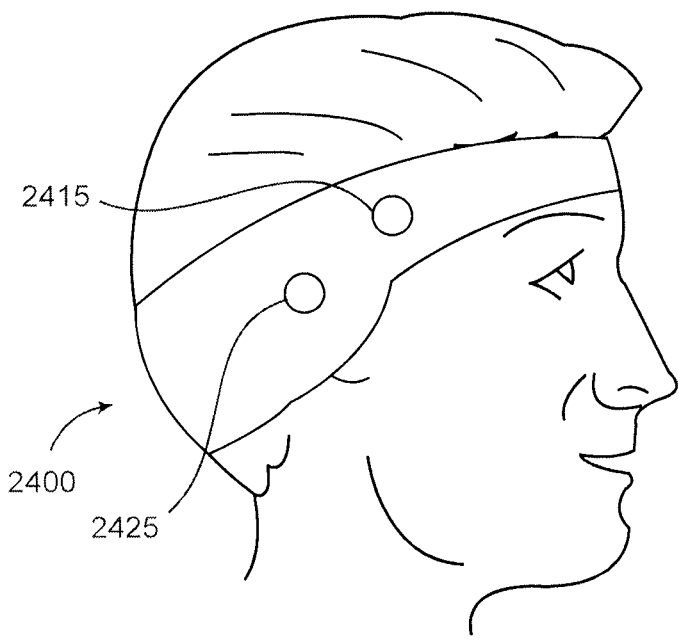
FIGS. 24a and 24b show another embodiment of a System For Reducing Subconscious Neuromuscular Tension in the form of a headband.
Figure 24B:
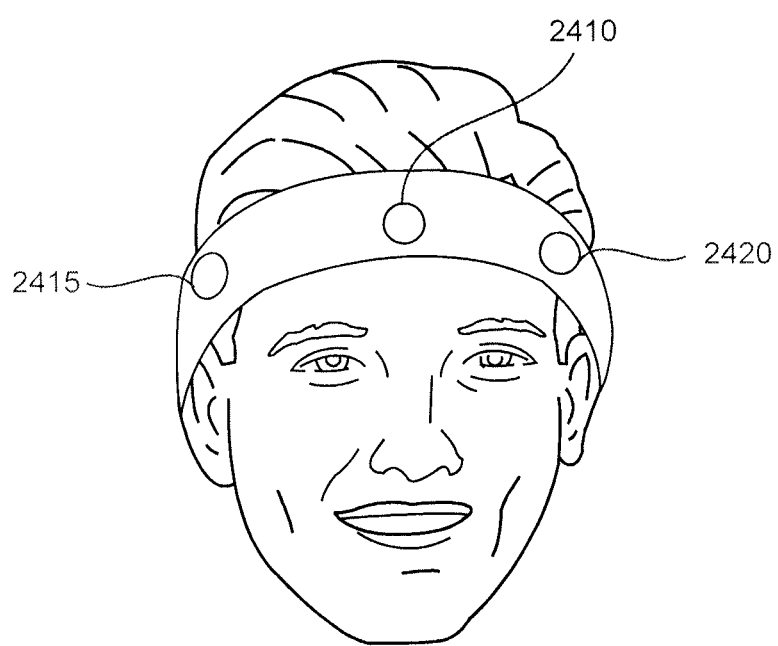

FIG. 24 shows another embodiment of a headband 2400 System For Reducing Subconscious Neuromuscular Tension. It has three electrodes across the forehead, ground 2410, and positive 2415 and negative 2420 electrodes. The positive 2415 and negative 2420 electrodes would rest on the Frontalis and/or procerus muscles on either side. In the headband over the ears are soft speakers 2425 that would play a sound to alert the user when they are clenching. The electronics are housed in the back of headband at the back of the head. In some options, the headband is a soft cloth material and may be semi-elastic.

Figure 25:
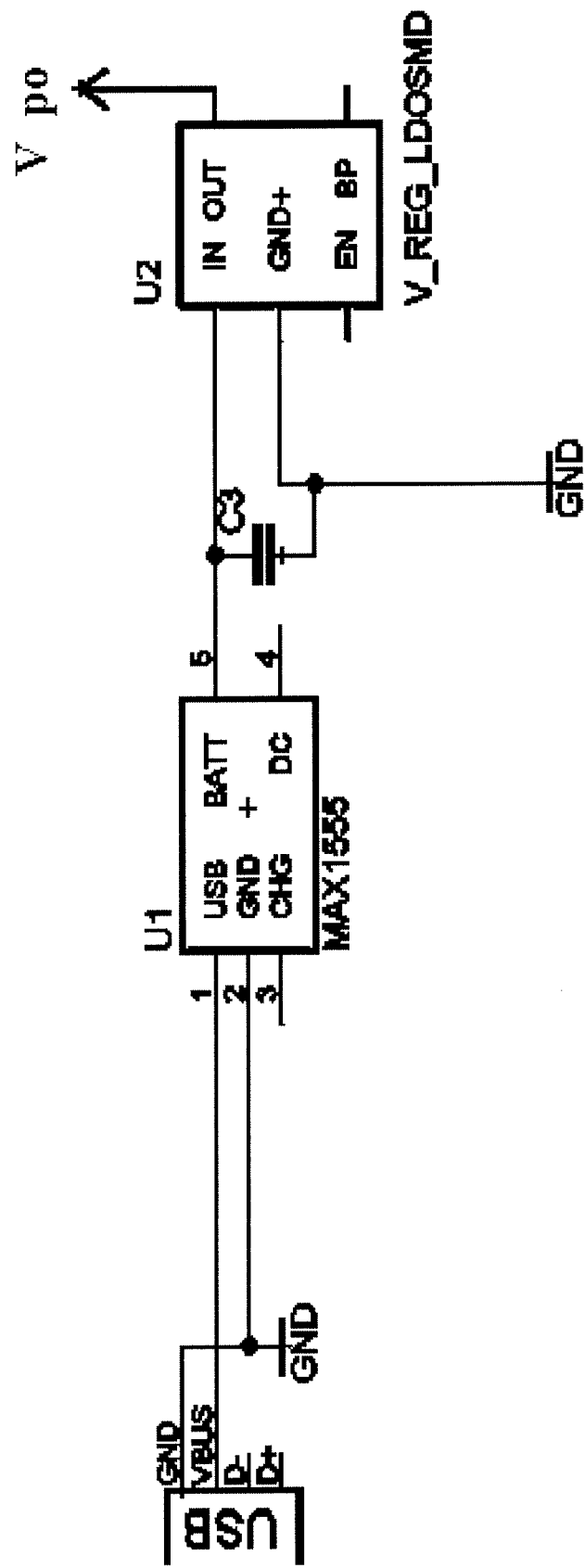
FIG. 25 shows one embodiment of a battery charging/voltage regulating schematic.

FIG. 25 shows one embodiment of a battery charging/voltage regulating schematic showing a USB input, a battery, and voltage control circuitry.

Figure 26A:
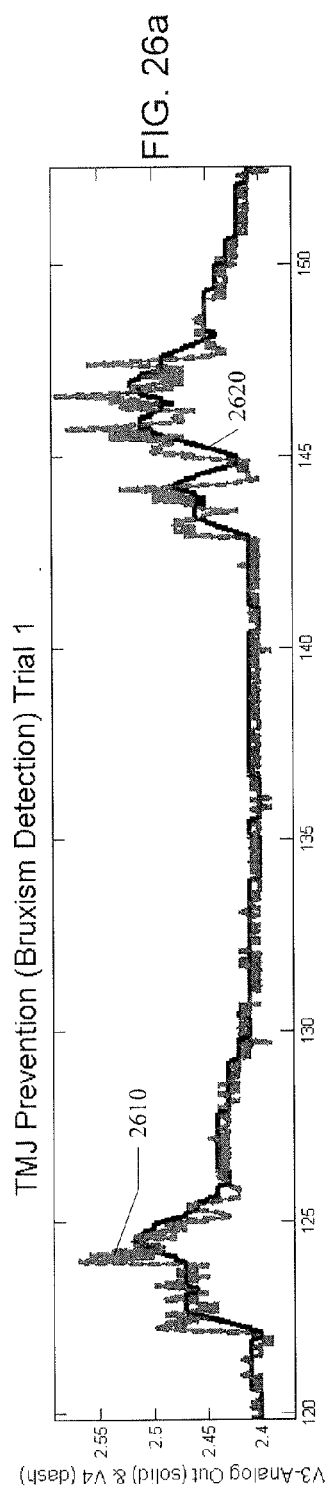
FIGS. 26a-c show graphs of the signals generated by an embodiment of the system.
Figure 26B:
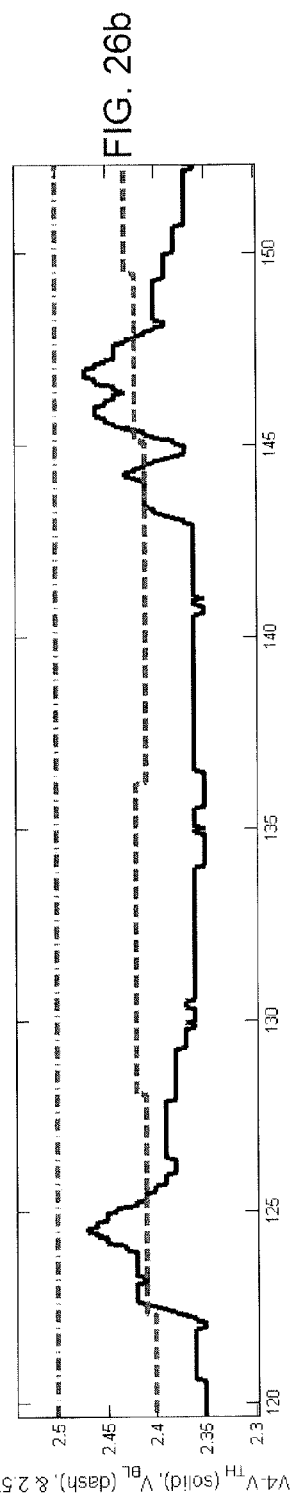
Figure 26C:
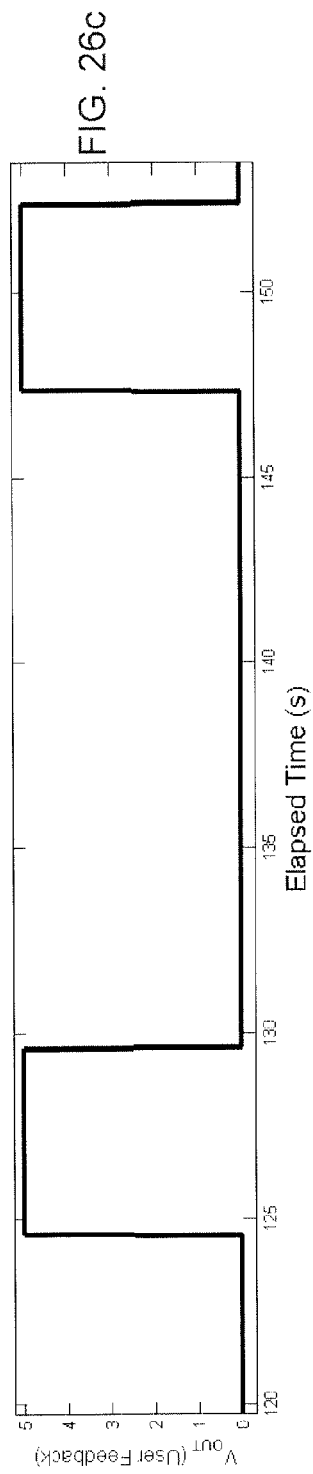

FIGS. 26a-c show graphs of Bruxism detection. FIG. 26a shows the Analog output after the envelope follower 2610 and Ring-buffered output 2520 interpreted as an analog signal (smoother than 2610). FIG. 26b shows TH compared to V_BL (larger ring buffer) and 2.5V showing the inadequacy of the static "base-line" and the obvious points indicating "bruxing". FIG. 26c shows the actual value of the feedback (digital output represented as logic HIGH)

Another alternative includes the ability to connect an MP3 device to the headband to either constantly play relaxing music or relaxation tapes, or have it come on only when the user is clenching. This same design can be implemented for a hat and visor as well, where the electrodes are in the brim and go across the forehead.

In any of the embodiments, the system may further include a data collection system, that either stores data within the device for later download or transmission or concurrently transmits data to another device for storage (smart phone, etc.), or both. The system may record times of the day that clenching events occur in order to detect problem times. The length, frequency, and other features of clenching events may be recorded. The response time by the user to the indicator indicating a clenching event may be recorded and the intensity of the indicator may be automatically or manually adjusted (volume, light level, vibration strength) according to the response time. The system may record the progress of the user in relation to clenching events. Software may accompany the system and may be configurable to work with a computer, smart phone or other computing device.

Various design features of the various embodiments above may be mixed and matched as will be apparent to one skilled in the art in light of this disclosure. For example, sensor placement in the various embodiments may be substituted into any one of the other embodiments. Also, the notification methodology in the various embodiments (visual, auditory, vibration) may be substituted into the any one of the other embodiments.

The foregoing description of the embodiments of the Systems And Methods For Reducing Involuntary Neuromuscular Tension Including Bruxism has been presented only for the purpose of illustration and description and is not intended to be exhaustive or limited to the precise forms disclosed. Numerous modifications and adaptations will be apparent to those skilled in the art without departing from the spirit and scope of this disclosure.

We claim:

1. A system for the detection of bruxism, comprising:
   an electronics housing configured to be worn on a head of a user;
   a first sensor and a second sensor, located on a side of the electronics housing, such that the first and second sensors are configured to be secured firmly to the face of the user using an adhesive portion, the first and second sensors positioned a distance apart from each other and positioned to rest over a muscle of the face, the distance apart being such that the first and second sensors both rest on the muscle of the face;
   a feedback generator, configured to provide feedback to the user when a clench event occurs;
   a microprocessor, the microprocessor configured to execute programming receive a plurality of inputs from the first and second sensors, determine when the clench event occurs based on the plurality of inputs from the first and second sensors, and activate the feedback generator to provide the feedback to the user upon an occurrence of the clench event; and
   a ground sensor configured to provide a second plurality of inputs to the microprocessor and wherein the ground is configured to be located in a location on the face of the user where there are few muscle fibers, wherein the electronics housing includes the first and second sensors but not the microprocessor and feedback generator.

2. The system of claim 1 wherein the ground sensor is placed a second distance from the first and second sensors, the second distance being greater than the distance between the first and second sensors.

3. The system of claim 1 wherein the feedback generator is a small unbalanced motor.

4. The system of claim 1 wherein the microprocessor includes logic for providing a ring buffer, wherein the ring buffer is used to determine an average for the plurality of inputs, and the average of the plurality of inputs is compared to a threshold to determine the clench event.

5. The system of claim 1 wherein the muscle is the masseter muscle.

6. The system of claim 1 wherein the muscle is the temporalis muscle.

7. The system of claim 1 wherein the muscle is the Frontalis muscles.

8. The system of claim 1 wherein the muscle is the trapezius muscle.

9. The system of claim 1 wherein the muscle is the sternocleidomastoid.

10. The system of claim 1 wherein the electronics housing includes a wireless network communication system.

11. The system of claim 1 wherein the electronics housing is included as part of a pair of glasses.

12. A method for the prediction of bruxism, the method comprising:
    (a) providing a Bruxism Detection System to a user, wherein the Bruxism Detection System includes a first, second, and third sensor, the third sensor being a ground sensor and the ground is configured to be located in a location on the face of the user where there are few muscle fibers;
    (b) calibrating the Bruxism Detection System, including providing a manual adjustment mechanism for the user;
    (c) monitoring the user with the Bruxism Detection System, wherein the monitoring includes smoothing the signal from a plurality of sensors;
    (d) detecting a clench event, including comparing a second electromyography signal to the clench event indicator;
    (e) providing feedback to the user based on the detecting of (d) via a feedback generator;
    (f) detecting a response time of the user to the feedback, the response time being a time for the user to stop the clench event; and
    (g) adjusting an intensity of the feedback based on the response time.

13. A system for the detection of bruxism, comprising:
    an electronics housing configured to be worn on a head of a user;
    a first sensor and a second sensor, located on a side of the electronics housing, such that the first and second sensors are configured to be secured firmly to the face of the user using an adhesive portion, the first and second sensors positioned a distance apart from each other and positioned to rest over a muscle of the face, the distance apart being such that the first and second sensors both rest on the muscle of the face;
    a feedback generator, configured to provide feedback to the user when a clench event occurs;
    a microprocessor, the microprocessor configured to execute programming, receive a plurality of inputs from the first and second sensors, determine when the clench event occurs based on the plurality of inputs from the first and second sensors, and activate the feedback generator to provide the feedback to the user upon an occurrence of the clench event; and
    a ground sensor configured to provide a second plurality of inputs to the microprocessor and wherein the ground is configured to be located in a location on the face of the user where there are few muscle fibers, wherein the microprocessor is configured to monitor a response time of the user to the feedback, the response time being a time for the user to stop a clench and wherein the feedback has an intensity, and the intensity of the feedback is automatically adjusted according to the response time.

14. A system for the detection of bruxism, comprising:
    an electronics housing configured to be worn on a head of a user;
    a first sensor and a second sensor, located on a side of the electronics housing, such that the first and second sensors are configured to be secured firmly to the face of the user using an adhesive portion, the first and second sensors positioned a distance apart from each other and positioned to rest over a muscle of the face, the distance apart being such that the first and second sensors both rest on the muscle of the face;
    a feedback generator, configured to provide feedback to the user when a clench event occurs;
    a microprocessor, the microprocessor configured to receive a plurality of inputs from the first and second sensors, determine when the clench event occurs based on the plurality of inputs from the first and second sensors, and activate the feedback generator to provide the feedback to the user upon an occurrence of the clench event;

a ground sensor configured to provide a second plurality of inputs to the microprocessor and wherein the ground is configured to be located in a location on the face of the user where there are few muscle fibers; and wherein the microprocessor is configured to execute programming that monitors a response time of the user to the feedback, the response time being a time for the user to stop a clench and wherein the feedback has an intensity, and the intensity of the feedback is automatically adjusted according to the response time.

15. The system of claim 14, wherein the location is behind the ear of the user.

16. The system of claim 14 wherein the electronics housing includes the first and second sensors but not the microprocessor and feedback generator.

17. A system for the detection of bruxism, comprising:

an electronics housing configured to be worn on a head of a user;

a first sensor and a second sensor, located on a side of the electronics housing, such that the first and second sensors are configured to be secured firmly to the face of the user using an adhesive portion, the first and second sensors positioned a distance apart from each other and positioned to rest over a muscle of the face, the distance apart being such that the first and second sensors both rest on the muscle of the face;

a feedback generator, configured to provide feedback to the user when a clench event occurs;

a microprocessor, the microprocessor configured to execute programming, receive a plurality of inputs from the first and second sensors, determine when the clench event occurs based on the plurality of inputs from the first and second sensors, and activate the feedback generator to provide the feedback to the user upon an occurrence of the clench event; and a ground sensor configured to provide a second plurality of inputs to the microprocessor and wherein the ground is configured to be located in a location on the face of the user where there are few muscle fibers, wherein the microprocessor is configured execute programming that monitors a response time of the user to the feedback, the response time being a time for the user to stop a clench and wherein the feedback has an intensity, and the intensity of the feedback is automatically adjusted according to the response time.

* * * * *